United States Patent
Hong et al.

(10) Patent No.: US 9,752,167 B2
(45) Date of Patent: *Sep. 5, 2017

(54) METHODS FOR PRODUCTION OF L-METHIONINE AND RELATED PRODUCTS

(71) Applicant: CJ CHEILJEDANG CORPORATION, Seoul (KR)

(72) Inventors: Soon Won Hong, Seoul (KR); In Seok Hwang, Seoul (KR); Sang Mok Lee, Seoul (KR); Youn Jae Lee, Seoul (KR); Jun Young Jung, Gyeonggi-do (KR); Aharon Eyal, Jerusalem (IL)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/982,108

(22) Filed: Dec. 29, 2015

(65) Prior Publication Data

US 2016/0108445 A1    Apr. 21, 2016

Related U.S. Application Data

(63) Continuation of application No. 13/339,441, filed on Dec. 29, 2011, now Pat. No. 9,260,732.

(60) Provisional application No. 61/428,171, filed on Dec. 29, 2010, provisional application No. 61/562,694, filed on Nov. 22, 2011.

(51) Int. Cl.
| | |
|---|---|
| *C12P 13/12* | (2006.01) |
| *C12P 11/00* | (2006.01) |
| *C05C 3/00* | (2006.01) |
| *C12P 7/46* | (2006.01) |
| *C12P 7/54* | (2006.01) |
| *C12P 13/06* | (2006.01) |
| *C07C 323/58* | (2006.01) |
| *A23L 33/175* | (2016.01) |

(52) U.S. Cl.
CPC ............. *C12P 13/12* (2013.01); *A23L 33/175* (2016.08); *C05C 3/00* (2013.01); *C07C 323/58* (2013.01); *C12P 7/46* (2013.01); *C12P 7/54* (2013.01); *C12P 11/00* (2013.01); *C12P 13/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2,867,655 A | 1/1959 | Othmer | |
| 3,709,666 A | 1/1973 | Van Westerveld et al. | |
| 5,068,188 A | 11/1991 | Wise et al. | |
| 5,168,055 A * | 12/1992 | Datta | ...................... C07C 51/02 435/145 |
| 7,223,884 B2 | 5/2007 | Kawabe et al. | |
| 7,611,873 B1 | 11/2009 | Usuda et al. | |
| 7,785,846 B2 | 8/2010 | Boy et al. | |
| 8,426,171 B2 | 4/2013 | Kim et al. | |
| 2005/0054060 A1 | 3/2005 | Chateau et al. | |
| 2012/0136058 A1 | 5/2012 | Kim et al. | |

FOREIGN PATENT DOCUMENTS

| | | |
|---|---|---|
| CN | 1894417 A | 1/2007 |
| CN | 101356281 A | 1/2009 |
| EP | 2 402 453 A2 | 1/2012 |
| JP | 58024890 B | 8/1966 |
| JP | 04244056 A | 9/1992 |
| JP | 2000-139471 A | 5/2000 |
| JP | 2007-514430 A | 6/2007 |
| KR | 10-2008-0011132 A | 1/2008 |
| KR | 10-0889434 B1 | 3/2009 |
| KR | 10-0905381 B1 | 6/2009 |
| KR | 10-2010-0097783 A | 9/2010 |
| WO | 90/15874 A1 | 12/1990 |
| WO | 2005/007862 A2 | 1/2005 |
| WO | 2005/059155 A2 | 6/2005 |
| WO | 2008/013432 A1 | 1/2008 |
| WO | 2008/127240 A1 | 10/2008 |
| WO | 2010/098629 A2 | 9/2010 |
| WO | 2010/098632 A2 | 9/2010 |
| WO | 2011/045377 A1 | 4/2011 |
| WO | WO2005007862 A2 * | 1/2015 |

OTHER PUBLICATIONS

Hwang et al. "Corynebacterium glutamicum Utilizes both Trans-sulfuration and Direct Sulfhydrylation Pathways for Methionine Biosynthesis" J. Bacteriol. 2002, 184, 1277-1286.*
Song et al. "Production of succinic acid by bacterial fermentation" Enzyme and Microbial Technology 39 (2006) 352-361.*
Weier et al. "Recovery of Propionic and Acetic Acids from Fermentation Broth by Electrodialysis" Biotechnol. Prog. 1992, 8, 479-485.*
Fuertes et al. (Apr. 21, 2011) "Methionine-rich composition for feeding animals," WO 2011/045377 A1. English machine translation obtained from the Internet via Espacenet at www.epo.org.
Jin et al. (2010) "Resolution of methionine by immobilized N-acetylornithine deacetylase," Chinese Journal of Bioprocess Engineering. 8:45-50.—English abstract only.
Katikaneni et al. (2002) "Purification of Fermentation-Derived Acetic Acid by Liquid-Liquid Extraction and Esterification," Ind. Eng. Chem. Res. 41:2745-2752.

(Continued)

*Primary Examiner* — Thane Underdahl
(74) *Attorney, Agent, or Firm* — Lathrop Gage LLP

(57) ABSTRACT

A method comprising: (a) enzymatically processing an O-acetylhomoserine (OAHS) fermentation liquor to produce L-methionine and an acetate source; (b) separating at least a portion of said L-methionine from at least a fraction of said acetate source to form separated L-methionine and a residual liquor comprising an acetate-source; and (c) recovering at least a portion of said acetate source from said residual liquor as recovered acetate.

11 Claims, 12 Drawing Sheets

(56) References Cited

OTHER PUBLICATIONS

Mizuno et al. (Sep. 1, 1992) "Production of methionine," JP H04-244056. English translation of the Abstract. (obtained from DERWENT).
Sumimoto Chemical Co. (Aug. 25, 1966) "Method for crystallizing DL-methionine," JP S68-024890 B. English ranslation of the Abstract. (obtained from DERWENT).
Young et al. (Sep. 6, 2010) "A method of enhancing the methionine solubility using mineral addition and acid reatment," KR 10-2010-0097783 A. English machine translation obtained from the Internet via Espacenet at www.epo.org.
International Search Report with Written Opinion corresponding to International Patent Application No. PCT/KR2011/010288, mailed Aug. 9, 2012.
Supplementary European Search Report corresponding to European Patent Application No. 11852758.9, dated Mar. 24, 2016.

* cited by examiner

US 9,752,167 B2

METHODS FOR PRODUCTION OF L-METHIONINE AND RELATED PRODUCTS

RELATED APPLICATIONS

This application is a continuation of U.S. patent application Ser. No. 13/339,441, filed Dec. 29, 2011, which claims priority to U.S. provisional application Nos. 61/428,171 filed on Dec. 29, 2010, and 61/562,694 filed on Nov. 22, 2011. The contents of each of the aforementioned applications are incorporated herein by reference in their entirety.

FIELD OF THE INVENTION

The present invention relates to a method of producing methionine and its byproducts from precursor of methionine.

BACKGROUND

Methionine and cysteine are sulfur-containing proteinogenic amino acids. Methionine is an essential amino acid for monogastrics and finds a variety of applications in the food and medical industries. For example, methionine is used as an additive in animal feed and foods and as an ingredient in parenteral nutrient solutions and medicines.

Physiologically, methionine can be a precursor for choline (lecithin) and creatine and is used as a starting material for the synthesis of cysteine and taurine. Typically, chemically synthesized DL-methionine has been used in the market for additives for animal feed.

L-methionine has been produced by direct fermentation. However the low solubility of L-methionine can cause formation of crystals during direct fermentation to produce L-methionine. These crystals make it difficult to agitate the culture medium and may decrease fermentation yield. The sulfur required to produce L-methionine by direct fermentation can also adversely affect bacterial growth.

WO 2008/013432 describes a two-step process for producing L-methionine which includes the fermentative production of an L-methionine precursor (e.g., O-acetylhomoserine (OAHS) or O-succinyl homoserine (OSHS)) followed by the enzymatic conversion of the precursor to L-methionine.

When OAHS is the precursor, methyl mercaptan ($CH_3SH$) and OAHS react to produce acetate and methionine. When OSHS is the precursor, $CH_3SH$ and OSHS react to produce succinate and methionine.

The $CH_3S$-residue of methyl mercaptan is substituted with succinate or acetate residue of OSHS or OAHS to produce methionine. Methyl mercaptan ($CH_3SH$) can be added in different forms during the reaction.

SUMMARY OF THE INVENTION

A broad aspect of the invention relates to industrial scale production of L-methionine from a methionine precursor such as O-acetylhomoserine (OAHS) or O-succinylhomoserine (OSHS).

One aspect of some embodiments of the invention relates to recovery of carbon and/or nitrogen. This recovery can occur at one or more stages during the production process.

In some exemplary embodiments of the invention, carbon and nitrogen are recovered together, for example as ammonium acetate. Optionally, the recovered carbon and/or nitrogen are recycled to a fermentor or to another upstream production process.

One aspect of some embodiments of the invention relates to recovery of L-methionine from enzymatically processed fermentation liquor.

In some exemplary embodiments of the invention, recovery is by crystallization, optionally in two rounds. The term "fermentation liquor" as used in this specification and the accompanying claims indicates a culture medium which has been used as a fermentation substrate and from which cells have been removed.

In some embodiments of the invention, this liquor contains an L-methionine precursor. Optionally, the liquor is treated with activated carbon and/or filtered and/or concentrated by evaporation prior to crystallization. In some exemplary embodiments of the invention, crystallization is induced by evaporation and/or addition of an organic solvent to the liquor. According to various exemplary embodiments of the invention the solvent includes an alcohol such as methanol or ethanol.

As used in this specification and the accompanying claims, the term "mother liquor" indicates enzymatically processed fermentation liquor which has been subjected to one round of methionine removal (e.g., by crystallization).

In some exemplary embodiments of the invention, a second round of removal (e.g., crystallization) is conducted on the mother liquor to produce a second crop of methionine crystals and "purged mother liquor".

As used in this specification and the accompanying claims, the term "purged mother liquor" indicates the mother liquor which has been subjected to an additional round of methionine crystallization and separated from the resultant crystals.

In some exemplary embodiments of the invention, this second round of crystallization relies upon distillation optionally followed by cooling. Optionally, distillation recovers organic solvent (e.g., methanol) from the mother liquor and/or purged mother liquor. In some exemplary embodiments of the invention, the recovered organic solvent is used to contribute to a crystallization of a first crop of methionine crystals.

Another aspect of some embodiments of the invention relates to compositions including L-methionine produced by the recovery process described above.

In some exemplary embodiments of the invention, the L-methionine is characterized by a ratio of carbon-14 to carbon-12 of at least $2.0 \times 10^{-13}$. In some exemplary embodiments of the invention, a ratio of L-methionine to D-methionine is at least 9:1, optionally 9.5:1, optionally 9.9:1, and optionally 9.99:1. Optionally, the L-methionine is substantially enantiomerically pure.

In some exemplary embodiments of the invention, the composition includes crystalline L-methionine. According to various exemplary embodiments of the invention, characteristic impurities can be used to establish that L-methionine was produced by a process as described above. Characteristic impurities include but are not limited to, non-methionine amino acids, vitamins, minerals, ammonia, acetic acid, succinic acid, methyl mercaptan, enzymes and OAHS or OSHS. Depending upon the specific composition and the specific impurity in question, concentrations as low as 5000 PPM, optionally 1000 PPM, optionally 100 PPM, optionally 50 PPM, optionally 20 PPM, optionally 10 PPM, optionally 5 PPM, optionally 1 PPM, optionally 500 PPB, optionally 100 PPB, optionally 50 PPB, optionally 20 PPB, optionally 10 PPB, optionally 5 PPB, optionally 1 PPB or intermediate or lower concentrations may be sufficient to establish that L-methionine, whether provided in pure form, or as part of a composition, was produced by a process as described above.

In some exemplary embodiments of the invention, the composition is provided as an edible product such as, for example, a nutraceutical, a food product, an animal feed or an ingredient of such an edible product.

In other exemplary embodiments of the invention, the composition is provided as a complex including a heavy metal.

Another aspect of some embodiments of the invention relates to the dissolving of the second crop of L-methionine crystals and addition of the resultant methionine solution to a subsequent batch of enzymatically processed fermentation liquor.

In some exemplary embodiments of the invention, the dissolved second crop of methionine is purified to some degree by activated carbon treatment and/or filtration and/or re-crystallization together with a subsequent batch of enzymatically processed culture liquor or prior to such addition.

Another aspect of some embodiments of the invention relates to acidulation of residual liquor followed by extraction with an extractant including an organic solvent to recover acetic acid.

According to various exemplary embodiments of the invention, the "mother liquor" and/or the "purged mother liquor" can serve as the residual liquor which is acidulated. Optionally, two rounds of acidulation are conducted.

In some exemplary embodiments of the invention, the organic solvent includes an acetate ester. Optionally, the solvent includes isobutyl acetate (IBA). According to these embodiments, extraction forms an acetic acid-comprising organic phase also referred to as an extract.

In some exemplary embodiments of the invention, acidulation includes addition of a strong mineral acid (e.g., sulfuric acid).

In other exemplary embodiments of the invention, acidulation includes addition of a carboxylic acid.

In other exemplary embodiments of the invention, acidulation includes contacting with $CO_2$ gas under pressure and contact with an acidic cation exchanger.

According to various exemplary embodiments of the invention, manipulation of the extract regenerates the extractant and produces a desired acetate product.

In some exemplary embodiments of the invention, the manipulation includes back extraction with ammonia and the acetate product is ammonium acetate.

In other exemplary embodiments of the invention, the manipulation includes back extraction with water and the extractant is regenerated while forming an aqueous acetic acid solution.

In other exemplary embodiments of the invention, the manipulation includes treatment with an alcohol and a corresponding acetate ester is produced. For example, treatment with ethanol produces ethyl acetate and treatment with methanol produces methyl acetate.

In other exemplary embodiments of the invention, distillation of the initial extract is used instead of back extraction as a means to recover the extractant and/or free acetic acid.

Another aspect of some embodiments of the invention relates to lime treatment of residual liquor (e.g., mother liquor or purged mother liquor). Optionally, the lime includes calcium oxide and/or calcium hydroxide. According to various exemplary embodiments of the invention, the liquor treated with lime can be the "mother liquor" or the "purged mother liquor" as defined hereinabove. Optionally, lime treatment is performed prior to acidulation. According to these exemplary embodiments of the invention, lime reacts with ammonium acetate in the liquor to produce free ammonia and calcium acetate.

In some exemplary embodiments of the invention, the liberated ammonia is reacted with methyl mercaptan to produce ammonium-methyl mercaptan. Optionally, ammonium-methyl mercaptan can be used as a sulfur source in the enzymatic processing of OAHS.

In some exemplary embodiments of the invention, the lime treated liquor is acidulated as described above. According to various exemplary embodiments of the invention, this acidulation produces a calcium salt according to the specific acid employed. For example, acidulation with sulfuric acid produces calcium sulfate, acidulation with phosphoric acid produces calcium phosphate, and acidulation with nitric acid produces calcium nitrate.

In some exemplary embodiments of the invention, an acid which produces an insoluble calcium salt is employed, e.g., sulfuric or phosphoric acid. Optionally, insoluble salts are easier to harvest because they precipitate.

In some exemplary embodiments of the invention, the resultant acidulated liquor is subject to extraction with an extractant including an organic solvent followed by manipulation of the resultant extract as described above.

Another aspect of some embodiments of the invention relates to recovery of ammonium sulfate as purified crystals, as ammonium sulfate crystallization mother liquor and/or as part of a residual liquid at the end of processing. Optionally, any of these materials or their combination can be used as a fertilizer.

It will be appreciated that the various aspects described above relate to the solution of technical problems related to improving a material balance in methionine and/or lysine production using fermentative processes.

Alternatively or additionally, it will be appreciated that the various aspects described above relate to the solution of technical problems related to production of useful by-products from methionine production using fermentative processes.

Various liquors described throughout this specification and/or mentioned in the accompanying claims contain one or more impurities. These impurities may include, but are not limited to amino acids, vitamins, minerals, ammonia, acetic acid, succinic acid, methyl mercaptan, enzymes, L-methionine precursor and combinations thereof.

In some exemplary embodiments of the invention, there is provided a method which includes;

(a) enzymatically processing an O-acetylhomoserine (OAHS) fermentation liquor to produce L-methionine and an acetate source;

(b) separating at least a portion of the L-methionine from at least a fraction of the acetate source to form separated L-methionine and a residual liquor comprising an acetate-source; and (c) recovering at least a portion of the acetate source from the residual liquor as recovered acetate.

Optionally, the method includes using the recovered acetate as a reagent.

Optionally, the using includes applying to the processing of OAHS fermentation liquor.

Optionally, the using includes adding the reagent as an ingredient in a fermentation medium.

Optionally, the using includes applying to production of a fermentation product.

Optionally, the fermentation product is selected from the group consisting of carboxylic and amino acids.

Optionally, the amino acids are selected from the group consisting of lysine, valine, threonine, tryptophan, arginine and methionine.

Optionally, the method includes implementing at least one process, selected from the group consisting of water removal, active carbon treatment, addition of a solute, pH adjustment, ion-exchange, membrane filtration and contacting with at least one water-soluble organic solvent, during the purification process, for example, between the enzymatic processing and the separating.

Optionally, the residual liquor includes a salt of a mineral acid.

Optionally, the salt of a mineral acid includes an ammonium salt.

Optionally, the residual liquor includes at least 1 PPM OAHS.

Optionally, the separated L-methionine includes at least 1 PPB OAHS.

Optionally, the separating includes crystallizing.

Optionally, the crystallizing includes contacting with at least one alcohol selected from the group consisting of C1-C4 alcohols.

Optionally, the crystallizing L-methionine from said crystallizing feed comprises the use of at least one of a crystal habit modifier and L-methionine seed crystals.

Optionally, crystalline L-methionine resulting from the crystallizing is characterized by at least one characteristic selected from the group consisting of:
 (i) purity greater than 95%;
 (ii) containing less than 1% acetate source;
 (iii) OAHS content greater than 1 PPM;
 (iv) content of at least one particular impurity is greater than 10 PPM;
 (v) less than 2% of D-methionine;
 (vi) carbon-14 to carbon-12 ratio of at least $2.0 \times 10^{-13}$.

Optionally, the separating includes at least two crystallization steps.

Optionally, crystalline L-methionine resulting from the second crystallizing is characterized by at least one of:
 (i) purity greater than 75%, optionally greater than 80%;
 (ii) containing less than 0.1% acetate source; and
 (iii) containing at least 1 PPM of OAHS.

Optionally, the residual liquor is characterized by one or more of:
 (i) a methionine concentration of at least 15 g/l, optionally at least 20 g/l, often about 25 g/l or more;
 (ii) an acetate concentration of at least 100 g/l; optionally at least 125 g/l; often about 150 g/l or more;
 (iii) total solids of at least 20%, optionally at least 22%, often about 25% or more;
 (iv) specific gravity in the range of 1.05 to 1.25, optionally about 1.15; and
 (v) ammonium sulfate concentration of at least 60 g/l, optionally at least 100 g/l, optionally about 150 g/l or more.

Optionally, crystalline L-methionine resulting from the second crystallizing is added as a solute between the enzymatic processing and the separating.

Optionally, the recovering includes forming residual liquor comprising free acetic acid and separating the free acetic acid.

Optionally, the forming residual liquor comprising free acetic acid includes contacting with a strong acid.

Optionally, the forming residual liquor comprising free acetic acid includes at least one of contacting with $CO_2$ under pressure and contacting with a cation-exchanger that is at least partially in free acid form.

Optionally, the forming residual liquor comprising free acetic and the separating free acetic acid are conducted simultaneously.

Optionally, the recovering includes distilling free acetic acid from the residual liquor.

Optionally, the method includes contacting a liquor comprising free acetic acid with an extractant to form an acetic acid-comprising extract and an acetic acid depleted residual liquor.

Optionally, the method includes recovery of acetate from the acetic acid-comprising extract to form recovered acetate.

Optionally, the method includes contacting the acetic acid-comprising extract with a base to form recovered acetate salt of the base.

Optionally, the method includes the residual liquor with a salt of a strong mineral acid with a water solubility of less than 5% wt.

Optionally, the residual liquor further includes an ammonium source, which is recovered from the residual liquor as recovered ammonium.

Optionally, the method includes contacting the residual liquor with a calcium base to form free-base ammonia and a calcium salt, and separating the free-base ammonia to form recovered ammonium and separated ammonia-depleted residual liquor comprising a calcium salt.

Optionally, the method includes crystallizing an ammonium salt from the residual liquor to form crystalline ammonium salt and separated ammonia-depleted residual liquor.

Optionally, the method includes distilling ammonia and acetic acid from the residual liquor to form ammonia-depleted residual liquor.

Optionally, the method includes using at least a fraction of the recovered ammonia in production of a fermentation product.

Optionally, the method includes contacting the residual liquor with pressurized $CO_2$.

In some exemplary embodiments of the invention, there is provided a method for producing an L-methionine product comprising;
 (a) providing a fermentation liquor comprising an L-methionine precursor selected from the group consisting of O-acetylhomoserine and O-succinyl homoserine and at least one impurity;
 (b) enzymatically processing the precursor to produce a reaction liquor comprising L-methionine, an organic acid selected from the group consisting of acetic acid and succinic acid and at least one impurity;
 (c) modifying the reaction liquor to form a crystallizing feed; and
 (d) crystallizing L-methionine from the crystallizing feed to form crystalline L-methionine and an L-methionine-depleted mother liquor;
 wherein the crystalline L-methionine is characterized by at least one characteristic selected from the group consisting of:
 (i) purity greater than 95% purity;
 (ii) containing less than 1% organic acid;
 (iii) L-methionine precursor content greater than 1 PPM;
 (iv) content of at least one particular impurity greater than 10 PPM;
 (v) less than 2% of D-methionine; and
 (vi) carbon-14 to carbon-12 ratio of at least $2.0 \times 10^{-13}$.

Optionally, the modifying includes combining the reaction liquor with an L-methionine-comprising recycle stream.

Optionally, at least 85% of the amount of L-methionine in the reaction liquor is crystallized to crystalline L-methionine.

Optionally, the method includes the step of separating L-methionine from the mother liquor to form the L-methionine-comprising recycle stream and a purged mother liquor stream.

Optionally, the separating L-methionine from the mother liquor includes crystallization to form second crystalline L-methionine and separating of the second crystalline L-methionine from the purged mother liquor.

Optionally, the crystallizing L-methionine from the crystallizing feed includes the use of at least one of a crystal habit modifier and L-methionine seed crystals.

Optionally, one or more of the impurities is selected from the group consisting of amino acids, vitamins, minerals, ammonia, acetic acid, succinic acid, methyl mercaptan, enzymes, L-methionine precursor and a combination thereof.

Optionally, the method includes recovering at least a portion of the organic acid from the mother liquor as recovered organic acid.

Optionally, the method includes recovering at least a portion of the organic acid from the purged mother liquor as recovered organic acid.

Optionally, the enzymatic processing includes contacting with an anion exchanger and wherein at least a fraction of the organic acid is adsorbed on the anion exchanger.

Optionally, the L-methionine precursor is O-succinyl homoserine, wherein the organic acid is succinic acid and wherein the processing is conducted in the presence of calcium ions.

In some exemplary embodiments of the invention, there is provided a composition comprising L-methionine, characterized by at least one characteristic selected from the group consisting of:
(i) containing less than 1% organic acid;
(ii) L-methionine precursor content greater than 1 PPM, wherein the precursor is selected from OAHS and OSHS;
(iii) content of at least one particular impurity is greater than 10 PPM; and
(iv) carbon-14 to carbon-12 ratio of at least $2.0 \times 10^{-13}$.

Optionally, the composition is characterized by L-methionine purity greater than 95%.

Optionally, the composition is characterized by L-methionine containing less than 2% of D-methionine.

Optionally, the L-methionine includes crystalline L-methionine.

In some exemplary embodiments of the invention, there is provided a complex comprising a composition as described above and a heavy metal.

In some exemplary embodiments of the invention, there is provided a feed or food comprising a composition or complex as described above.

In some exemplary embodiments of the invention, there is provided a composition comprising an L-methionine, characterized by at least one characteristic selected from the group consisting of:
(i) amino acids other than methionine in a concentration of at least 0.05%, optionally at least 0.1%; optionally about 0.3% or more;
(ii) carboxylic acids in a concentration of at least 0.01%, optionally at least 0.03%, optionally at least 0.05%;
(iii) sulfate in a concentration of at least 0.2%, optionally at least 0.03%;
(iv) OAHS in a concentration of at least 1 PPB; and methionine purity of at least 60%, optionally at least 75%.

In some exemplary embodiments of the invention, there is provided a composition comprising L-methionine, characterized by at least one characteristic selected from the group consisting of:
(i) a methionine concentration of at least 15 g/l, optionally at least 20 g/l, optionally about 25 g/l or more;
(ii) an acetate concentration of at least 100 g/l; optionally at least 125 g/l; optionally about 150 g/l or more;
(iii) total solids of at least 20%, optionally about 25% or more; and
(iv) specific gravity in the range between 1.05 and 1.25, optionally about 1.15; and
(iv) ammonium sulfate concentration of at least 100 g/l, optionally at least 125 g/l, optionally about 150 g/l or more.

In some exemplary embodiments of the invention, there is provided a composition comprising L-methionine, characterized by at least one characteristic selected from the group consisting of:
(i) a methionine concentration of at least 100 g/l;
(ii) an OAHS concentration less than 0.1 g/l;
(iii) a detectable amount of at least one amino acid selected from the group consisting of Glutamic acid, Valine, Isoleucine, Leucine, Tyrosine, Phenylalanine, Threonine;
(iv) a mineral acid content of at least 30 g/l;
(v) an acetic acid content of at least 30 g/l; and
(vi) a concentration of carboxylic acids other than acetic acid of at least 0.05 g/l, optionally at least 0.1 g/l; and
(vii) a methanol concentration of at least 10% by weight.

In some exemplary embodiments of the invention, there is provided a composition comprising:
(i) at least 30% ammonium acetate;
(ii) at least 1 PPM of ammonium sulfate; and
(iii) at least 1 PPM of a compound selected from the group consisting of isobutanol, isobutyl acetate, acetamide and methionine.

In some exemplary embodiments of the invention, there is provided an ingredient of fermentation liquor comprising a composition as described above.

In some exemplary embodiments of the invention, there is provided a composition comprising at least 10%, optionally at least 12%, optionally at least 20%, optionally at least 30%, often 15% or more ammonium sulfate, at least 10 PPM of a compound selected from the group consisting of ammonium acetate, isobutanol, isobutyl acetate, acetamide and methionine.

In some exemplary embodiments of the invention, there is provided an ingredient of a fertilizer comprising a composition as described above.

In some exemplary embodiments of the invention, there is provided a composition comprising at least 90% isobutyl acetate, isobutanol and at least one of acetamide and acetic acid.

In some exemplary embodiments of the invention, there is provided a method comprising;
(a) enzymatically processing a fermentation liquor comprising an L-methionine precursor selected from the group consisting of O-acetylhomoserine and O-succinyl homoserine to produce L-methionine and a source of an organic acid selected from acetic acid and succinic acid;
(b) separating at least a portion of the L-methionine from at least a fraction of the source of organic acid to form separated L-methionine and a residual liquor comprising a source of organic acid,
(c) recovering at least a portion of the source of organic acid from the residual liquor as recovered organic acid.

Optionally, the method includes using the recovered organic acid as a reagent.

Optionally, the using includes applying a fermentation product to the production. Optionally, the fermentation product is selected from the group consisting of carboxylic and amino acids.

Optionally, the amino acids are selected from the group consisting of lysine, valine, threonine, tryptophan, arginine and methionine.

Optionally, the using includes applying a fermentation liquor to the processing.

Optionally, using includes adding the reagent as an ingredient in a fermentation medium.

Optionally, the L-methionine precursor is O-succinyl homoserine, wherein the organic acid is succinic acid, and wherein recovering includes forming residual liquor comprising free succinic acid and separating the free succinic acid.

Optionally, the separating of the free succinic acid includes crystallizing the free succinic acid.

Optionally, the recovering includes crystallizing calcium succinate.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

Percentages (%) of chemicals typically supplied as powders or crystals (e.g., methionine and ammonium sulfate crystal) are w/w (weight per weight) unless otherwise indicated.

Percentages (%) of chemicals typically supplied as liquids (e.g., ethanol, and/or methanol, and/or ammonium acetate) are w/w (weight per weight) unless otherwise indicated.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF THE INVENTION

Some exemplary embodiments of the invention relate to methods for producing L-methionine from a fermentation liquor containing a methionine precursor. Other embodiments relate to L-methionine produced by such methods and products containing such L-methionine. Additional embodiments of the invention relate to methods for producing, or recovering, non-methionine byproducts.

Specifically, some embodiments of the invention can be used to harvest chemicals (e.g., salts and/or esters) which can be used as ingredients in a culture media.

The principles and operation of methods and/or compositions and/or products according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Exemplary Acetate Recovery Method

Figure 1:
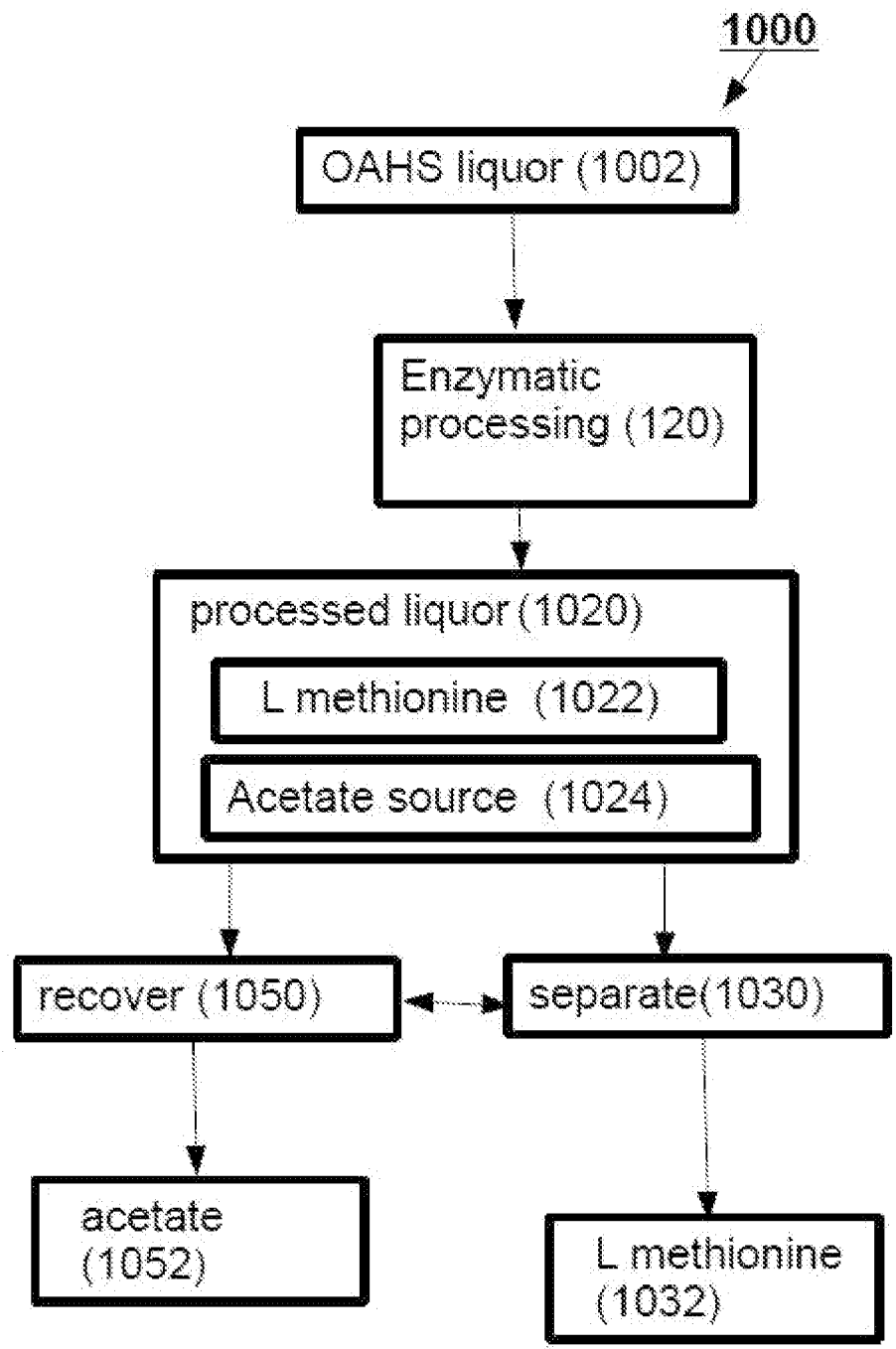
FIG. 1 is a schematic overview of a process for recovering acetate during methionine purification according to some exemplary embodiments of the invention.

FIG. 1 is a simplified flow diagram of a method for acetate recovery indicated generally as 1000. Depicted exemplary method 1000 includes enzymatically processing 120 a fermentation liquor 1002 containing O-acetylhomoserine (OAHS) to produce a processed liquor 1020 comprising L-methionine 1022 and an acetate source 1024.

Enzymatic processing may be, for example, as described in WO 2008/013432 A1 which is fully incorporated herein by reference.

Depicted exemplary method 1000 includes separating 1030 at least a portion of L-methionine 1022 from at least a fraction of acetate source 1024 to form separated L-methionine 1032 and a residual liquor comprising an acetate-source 1024 and recovering 1050 at least a portion of acetate source 1024 from liquor 1020 as recovered acetate 1052. According to various exemplary embodiments of the invention recovered acetate 1052 can be in various forms.

Depicted exemplary method 1000 can be described more generally as enzymatically processing 120 an O-acetylhomoserine (OAHS) fermentation liquor 1002 to produce L-methionine 1022 and an acetate source 1024. The depicted method includes separating 1030 at least a portion of L-methionine 1032 and recovering 1050 at least a portion of acetate source 1024 as recovered acetate 1052.

According to various exemplary embodiments of the invention processing 120, recovering 1050 and separating 1030 can be performed in any feasible order and/or simultaneously.

In one exemplary embodiment of the invention, an OAHS concentration in liquor 1002 is about 180 to 200 g/l and is diluted prior to enzymatic processing 120 (e.g., to about (70 to 110 g/l). After processing 120, the OAHS concentration drops dramatically, for example to about ≤0.1% w/w, i.e., about ≤0.5 g/l.

Methionine is less soluble than OAHS (53.7 (20° C.) g/l in water for 1-methionine vs. ~200 g/l in water (25° C.) for OAHS (see http://www.chemspider.com/ChemicalStructure.513.html). In some exemplary embodiments of the invention, this dilution contributes to a reduction in unwanted precipitation of methionine.

According to various exemplary embodiments of the invention this dilution is achieved by addition of water and/or reagent solutions to liquor 1002 prior to processing 120.

In some exemplary embodiments of the invention, concentration of methionine 1022 in processed liquor 1020 is 65 to 75 g/l, optionally about 73 to 75 g/l. In some embodiments, methionine is maintained in solution at a high concentration by maintaining the solution at a temperature of 40, 45, 50, 55 or 60° C. or intermediate or higher temperatures. Alternatively or additionally, other solutes may contribute to an increase in methionine solubility.

Optionally, one or more of pH adjustment, providing methyl mercaptan, providing a base, providing enzymes of cells, incubation, an additional pH change and cell separation are conducted on liquor 1002 prior to processing 120.

According to various exemplary embodiments of the invention a salt of methyl mercaptan used in enzymatic processing 120 can be fresh and/or recycled. In some exemplary embodiments of the invention, methyl mercaptan is provided as an ammonium salt. Alternatively, or in addition to, methyl mercaptan in acid form and ammonia are supplied separately. Optionally, the methyl mercaptan/OAHS ratio is 1.01 (mole to mole). In some exemplary embodiments of the invention, recycling includes stripping of residual methyl mercaptan and absorbing to ammonia solution and recycling to enzymatic processing 120.

According to various exemplary embodiments of the invention acetate source 1024 includes acetic acid and/or an acetate salt (optionally ammonium acetate) and/or an acetate ester.

In some exemplary embodiments of the invention, separating 1030 occurs prior to recovering 1050.

In other exemplary embodiments of the invention, acetate source 1024 is recovered 1050 prior to separation 1030 (e.g., on an anion exchanger).

For example, in some exemplary embodiments of the invention, methyl mercaptan is introduced in its free acid form ($CH_3SH$) and acetic (in other exemplary embodiments of the invention, succinic) acid is generated in its free acid form. In some embodiments, the reaction takes place in the presence of a free-base anion exchanger, which is selected so that it adsorbs the acid as it forms thereby maintaining the pH at the required level. According to alternative embodiments, methyl mercaptan is provided while adsorbed on an anion exchanger and is exchanged for acetic acid (in other exemplary embodiments of the invention, for succinic acid) during the processing. According to these embodiments, after separation of the acid-loaded resin, methionine is crystallized from the reaction solution, which is now low in mineral salt. At this stage, the acid-loaded anion exchanger can be treated for regeneration and for the recovery of the acid or its product. In some exemplary embodiments of the invention, the anion-exchanger is thermally stable (e.g., Reilex type) and acetic acid (or succinic acid) is recovered from it by distillation (optionally, concentrated and pure) or by a reaction with an alcohol (e.g., ethanol) to form the corresponding ester (ethyl acetate).

In some exemplary embodiments of the invention, methionine 1032 is separated 1030 by crystallization. In that case, processed liquor 1020 becomes a mother liquor as defined hereinabove.

According to various exemplary embodiments of the invention, "acetate" in recovered acetate 1052 can be different from "acetate" in acetate source 1024. In some exemplary embodiments of the invention, acetate source 1024 contains acetate salt(s) while recovered acetate 1052 is free acetic acid, an acetate ester or a different acetate salt.

According to various exemplary embodiments of the invention acetate source 1024 includes acetic acid and/or an acetate salt (e.g., ammonium acetate) and/or an acetate ester. The acetyl group of acetate source 1024 can be derived from OAHS and/or from acetic acid added to processing 120. In some exemplary embodiments of the invention, ammonia methyl mercaptan serves as an ammonia source and acetate source 1024 includes ammonium acetate.

Optionally, enzymatic processing 120 is conducted at a pH in the range between 5.5 and 7, optionally in the range of pH of 6.2 to 6.5.

Figure 3:
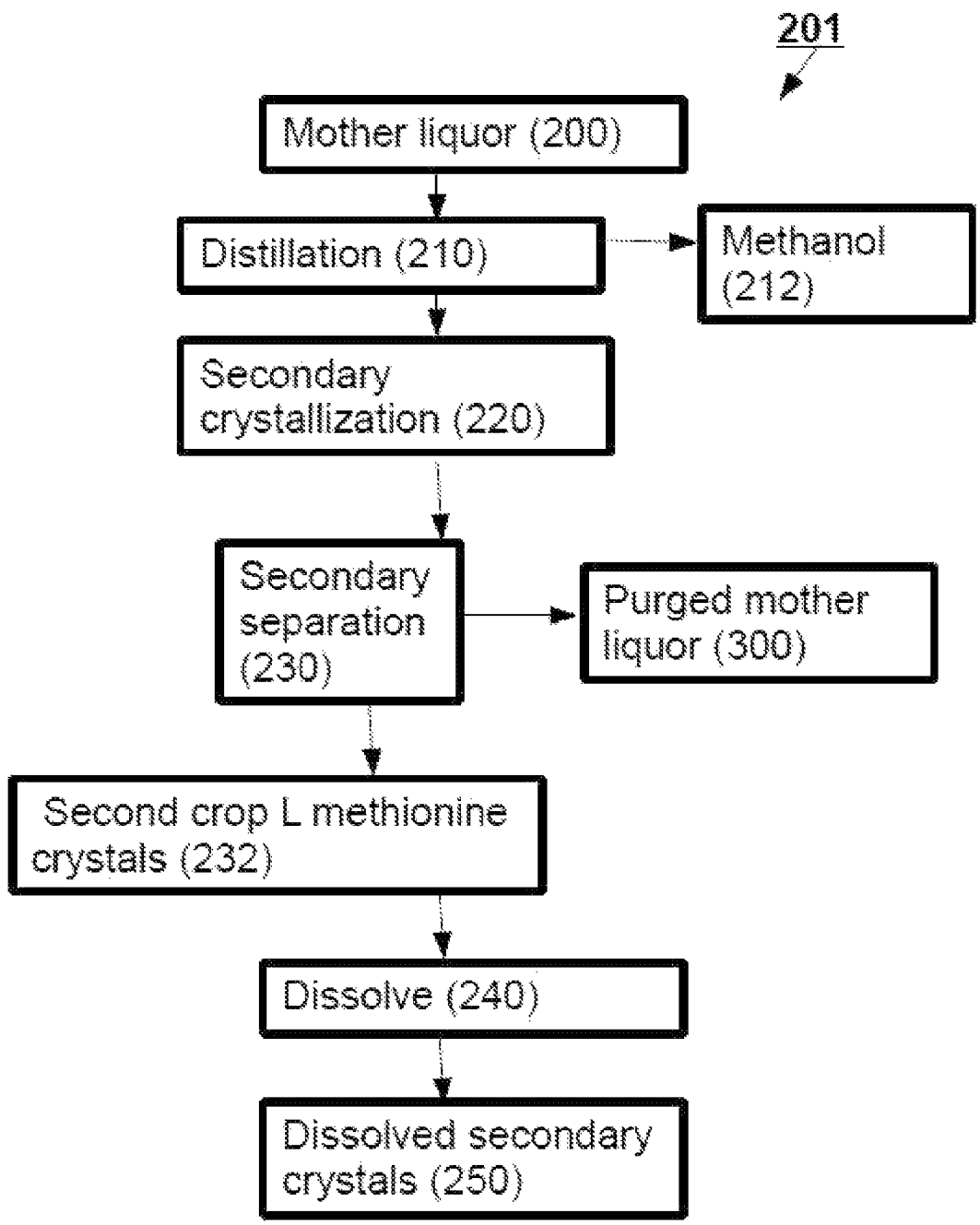

Optionally, additional L-methionine is removed from the mother liquor to form a purged mother liquor (FIG. 3).

In some exemplary embodiments of the invention, the mother liquor or the purged mother liquor is acidulated to produce an acidulated liquor (AL). Optionally, the acidulation includes addition of a strong mineral acid or a carboxylic acid to the relevant liquor. In some exemplary embodiments of the invention, the strong mineral acid includes sulfuric acid and/or phosphoric acid and/or nitric acid. Optionally, the carboxylic acid includes acetic acid.

Alternatively or additionally, acidulation includes contacting with $CO_2$ gas under pressure and contact with an acidic cation exchanger.

Figure 2:
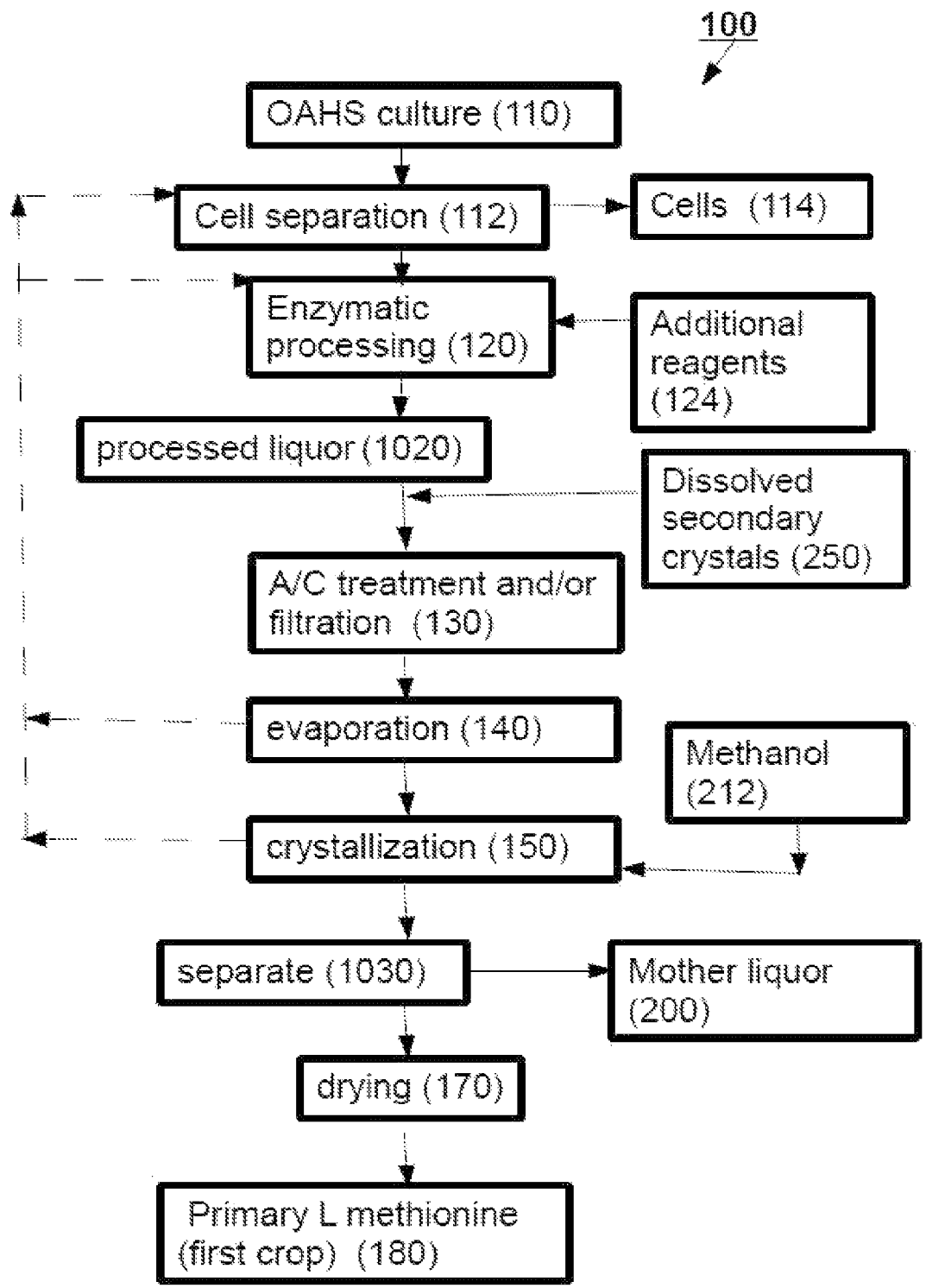
FIGS. 2, 3 and 4 provide a schematic overview of a process for producing L-methionine in accord with various exemplary embodiments of the invention.

In some exemplary embodiments of the invention, method 1000 includes using recovered acetate 1052 as a reagent (e.g., additional reagent 124; FIG. 2). Optionally, recovered acetate 1052 is used as a reagent in enzymatic processing 120.

Alternatively or additionally, recovered acetate 1052 can be used by adding it as an ingredient in a fermentation medium.

Fermentation medium as used here indicates a source of carbon (and other ingredients) to fermentation, while "fermentation liquor" is the fermentation-product comprising solution formed in such fermentation of the carbon source.

Alternatively or additionally, recovered acetate 1052 can be used in production of a fermentation product. Optionally, recovered acetate 1052 can be used in direct production of the product (e.g., lysine) or in producing a precursor to be further converted to such product (e.g., production of OAHS to be enzymatically processed to L-methionine).

Alternatively or additionally, recovered acetate 1052 can be used for pH adjustment during enzymatic processing 120 and/or cell separation (e.g., filtration) and/or in downstream processing (e.g., for pH adjustment or for elution of a compound adsorbed on a resin).

Optionally, the fermentation product includes carboxylic acids and/or amino acids (e.g., lysine and/or valine and/or threonine and/or tryptophan and/or arginine and/or methionine). Optionally, recovered acetate 1052 includes acetic acid which is used to adjust the pH of enzymatic processing 120 and/or cell separation and/or for purifying prior to the separating. Optionally, cell separation 112 (FIG. 2) and/or purifying (e.g., active carbon treatment 130; FIG. 2) is conducted at a pH in the range between 4.5 and 5.5, optionally at a pH of about 5. Alternatively or additionally, separating 1030 is conducted at pH in the range between 4.5 and 5.5, optionally at a pH of about 5.

In some embodiments (not diagrammed) enzymatic processing 120 employs microorganisms producing the relevant enzymes.

According to some of these embodiments, processing 120 may occur in culture 110 prior to cell separation 112 (e.g., if culture 110 includes microorganisms to produce OAHS and microorganisms that process OAHS to L-methionine or if culture 110 includes microorganisms which produce OAHS also process OAHS to L-methionine).

According to other embodiments in this category, processing 120 may include an additional round of culturing 110 with microorganisms that process OAHS to L-methionine followed by an additional round of separation 112.

According to still other embodiments in this category, microorganisms producing the relevant enzymes are cultured separately and a crude enzyme preparation is harvested from this separate culture. Optionally, the crude enzyme preparation is prepared from the used culture medium and/or from the cultured cells (i.e., culture supernatant and/or cell extract).

In some exemplary embodiments of the invention, a residual liquor (e.g., mother liquor and/or purged mother liquor) may be processed to remove impurities. Optionally, this processing includes acidulation. According to various exemplary embodiments of the invention acidulation can include addition of sulfuric acid and/or phosphoric acid and/or nitric acid and/or acetic acid.

Referring now to FIGS. 2 and 3, exemplary method 1000 can occur as part of an extended process. An exemplary extended process is depicted schematically in FIGS. 2 and 3 indicated generally as 100 and 201, respectively.

Depicted embodiment 100 begins with an OAHS culture 110 from which cells 114 are initially separated 112 to form a liquor 1002 which is enzymatically processed 120 to form processed liquor 1020 as described above. Separation 112 may be, for example, by centrifugation and/or filtration.

Enzymatic processing 120 of OAHS to methionine releases an acetyl group. According to various exemplary embodiments of the invention additional reagents 124 provided during enzymatic processing 120 are selected in consideration of the possibility of recovering non-methionine products in general, and acetyl-products in particular during downstream processes. Alternatively or additionally, in some exemplary embodiments of the invention, additional reagents 124 add ammonia and/or sulfate to liquor 1020.

Processed liquor 1020 contains myriad ingredients derived from cellular degradation in culture 110 and/or metabolites of ingredients of the growth media. Due to the complexity of the composition, a non-specific purification is optionally undertaken to reduce the total level of impurities without considering the concentration, or even presence, of any specific impurity in the liquor. In depicted method 100, this non-specific purification includes activated carbon treatment and/or filtration 130. This filtration can include, for example, membrane filtration. Optionally, water removal (e.g., evaporation 140) is conducted at this stage to increase the L-methionine concentration prior to crystallization 150.

Optionally, method 100 includes one or more of the following additional actions performed on liquor 1020 between enzymatically processing 120 and separating 1030: addition of a solute (e.g., dissolved secondary crystals 250), pH adjustment, ion-exchange, membrane filtration and contacting with at least one water-soluble organic solvent (e.g., methanol 212).

In those embodiments which employ activated carbon treatment, the pH during such treatment is optionally in the range of 4.5 to 6.0, in some cases about 5.0.

In some exemplary embodiments of the invention, the residual liquor (depicted as mother liquor 200) formed by separating 1030 includes a salt of a mineral acid. In some exemplary embodiments of the invention, the salt of a mineral acid includes an ammonium salt, optionally ammonium sulfate.

Optionally, the residual liquor (e.g., mother liquor 200) comprises OAHS. According to various exemplary embodiments of the invention, the concentration of OAHS in mother liquor 200 is at least 1, 5, 10, 20, 50 or 100 PPM or intermediate or greater concentrations.

Alternatively or additionally, separated L-methionine 1032 (or 180 in FIG. 2) comprises OAHS. According to various exemplary embodiments of the invention, the concentration of OAHS in separated L-methionine 1032 (or 180 in FIG. 2) is at least 1, 5, 10, 20, 50 or 100 PPM or intermediate or greater concentrations.

In some exemplary embodiments of the invention, separating 1030 includes crystallizing 150. In some exemplary embodiments of the invention, crystallizing 150 produce first, or primary, L-methionine crystals 180. Optionally, additional water is removed during crystallization 150.

In some exemplary embodiments of the invention, crystallizing 150 includes contact with at least one C1-C4 alcohol. Optionally, methanol and/or ethanol are employed for this purpose. Methanol 212 is depicted in FIG. 2. Optionally, methanol 212 is added at a ratio (w/w) of 15, 20, 25, 30 or 35% or intermediate or greater percentages to the feed to crystallization 150.

In some exemplary embodiments of the invention, 90, 95, 98.5, 99, 99.5% or intermediate or greater percentages of this methanol are recovered and available for reuse.

Optionally, water removed during evaporation 140 and/or crystallization 150 is recovered and re-used in an upstream process (e.g., cell separation 112 and/or enzymatic processing 120) as indicated by the dashed arrows. In some embodiments, crystals 180 resulting from crystallization 150 are dried.

According to various exemplary embodiments of the invention the yield of the first crop of L-methionine crystals 180 is greater than 85, 90, or even greater than 95% at this stage. This yield is calculated based on the amount of methionine 1022 formed by enzymatic processing 120. In some embodiments, the process is conducted cyclically and about 25, 30 or 35% of methionine in processed liquor 1020 goes to mother liquor 200 during separation 1030. Most of this material is recovered as dissolved secondary crystals 250.

Optionally, the first crop of crystalline L-methionine 180 is characterized by purity greater than 95, 96, 97, 98.5, 99 or even greater than 99.5%.

Alternatively or additionally, the first crop of crystalline L-methionine 180 is characterized by containing less than 1, 0.5, 0.25 or even less than 0.1% acetate source by weight.

Alternatively or additionally, the first crop of crystalline L-methionine 180 is characterized by an OAHS content greater than 1, 10, 20, 50 or even greater than 100 PPM or intermediate or greater concentrations.

Alternatively or additionally, the first crop of crystalline L-methionine 180 is characterized by a content of at least one particular impurity greater than 1, 10, 20, 50 or even greater than 100 PPM or intermediate or greater concentrations.

Alternatively or additionally, the first crop of crystalline L-methionine 180 is characterized by a content of less than 2, 1.5, 1, 0.5 or even less than 0.1% or intermediate concentrations of D-methionine. Optionally, the crystals are substantially enantiomerically pure.

Alternatively or additionally, the first crop of crystalline L-methionine 180 is characterized by a carbon-14 to carbon-12 ratio of at least $2.0 \times 10^{-13}$.

Alternatively or additionally, the first crop of crystalline L-methionine 180 is characterized by a concentration of less than 0.8, 0.6, 04, 0.2 or even less than 0.1% organic acid or intermediate or lower concentrations.

In some exemplary embodiments of the invention, crystals 180 are characterized by 2 or more of these characteristics.

In some exemplary embodiments of the invention, crystals 180 are characterized by 3 or more of these characteristics.

In some exemplary embodiments of the invention, crystals 180 are characterized by 4 or more of these characteristics.

In some exemplary embodiments of the invention, crystals 180 are characterized by 5 or more of these characteristics.

In some exemplary embodiments of the invention, separating 1030 comprises at least two processes. Optionally at least one of the two processes is crystallization 150. Alternatively or additionally, at least one of the two processes is ion-exchange.

In some exemplary embodiments of the invention, separating 1030 includes at least two crystallizations. Crystallization 150 forming first crop 180 has already been described. A second crystallization 220 producing a second crop of methionine crystals 232 is depicted in FIG. 3.

Optionally, a solvent (e.g., methanol and/or ethanol) is used in both crystallizations.

In some exemplary embodiments of the invention, the methionine concentration in the two crystallization feeds is similar. In some exemplary embodiments of the invention, distillation 210 of mother liquor 200 contributes to an increase in the methionine concentration in the feed stream to second crystallization 220.

In some embodiments, the methionine concentration in the crystallization feed streams is at least about 150 g/l.

In some exemplary embodiments of the invention, second crop 232 is 15, 20, 25, 27, 30, 32 or even 35% or more of first crop 180. In some exemplary embodiments of the invention, second crop 232 is dissolved 240 to form dissolved secondary crystals 250 which are reintroduced into the stream in FIG. 2 prior to 130.

In some exemplary embodiments of the invention, about 25% of methionine available for crystallization 150 (i.e., methionine 1022 plus dissolved secondary crystals 250 if added) remains in mother liquor 200 after separation 1030. According to various exemplary embodiments of the invention, of the methionine in mother liquor 200, about 3, 5, 10, 13 15 or 20% remains in purged liquor 300 after secondary separation 230. In some exemplary embodiments of the invention, methionine remaining in purged mother liquor is recovered in an additional downstream operation. Optionally, the additional downstream operation is performed on purged liquor 300 per se. In other exemplary embodiments of the invention, the additional downstream operation is performed on purged liquor 300 after purged liquor 300 has been further processed (e.g., by removal of ammonium and/or acetate and/or sulfate).

Optionally, the total crystal yield (i.e., 232 plus 180) is about 90% of methionine 1022 produced by enzymatic processing 120. Purity of crystals 180 can be 90, 95, 98, 99, 99.5 or substantially 100% or intermediate percentages.

In some embodiments, L-methionine crystals 232 are characterized by purity greater than 70, 75, 80, 85 or even greater than 90%.

In some embodiments, pH during crystallization 150 is in the range of 4.5 to 5.5, optionally about 5.0. Alternatively or additionally, in some embodiments, pH during crystallization 220 is in the range of 5.0 to 6.0, optionally about 5.5.

Alternatively or additionally, in some embodiments, L-methionine crystals 232 are characterized by containing less than 0.1% acetate source. In some embodiments, overall acetic acid recovery is 90, 93 or even 96% or more.

In some embodiments, L-methionine crystals 232 are characterized by an OAHS content less than 1. 0.5. 0.25 or 0.1% or lesser or intermediate concentrations.

Alternatively or additionally, in some embodiments, L-methionine crystals 232 are characterized by an OAHS content of at least 1, 5, 10, 20, 50 or even at least 100 PPM of OAHS.

In some embodiments, crystals 232 (optionally in dissolved form 250) are added as a solute between enzymatic processing 120 and separating 1030.

The liquid remaining after separation 230 is a residual liquor, indicated as purged mother liquor 300 (PML). Optionally, this residual liquor has a soluble solids content of about 23% and/or a specific gravity of about 1.14. The dissolved solids optionally include methionine (e.g., at about 15 to 35 g/l, optionally at about 25 to 35 g/l, optionally about 30 g/l) and/or acetate (e.g., at about 140-200 g/l, optionally about 162 g/l).

Alternatively or additionally, in some embodiments, a residual liquor formed by a method as described herein is characterized by at least one of: a methionine concentration of at least 25, 28, 31, 33 or even 35 g/l or more; an acetate concentration of at least 100, 120, 130, 140, 150, 160, 170 or even 180 g/l or more; total solids of at least 20, 23, 25, 23, 27, 30 or even 33% or more; specific gravity in the range 1.05 to 1.25, optionally 1.1 to 1.2, optionally about 1.15; and ammonium sulfate concentration of at least 60, 70, 80, 90, 100, 110, 120, 120, 130, 140 or even at least 150 g/l.

According to various exemplary embodiments of the invention, crystallizations 150 and 220 may differ with respect to temperature and/or methionine concentration and/or the composition of the solution from which the L-methionine is crystallized.

For example, an organic solvent (e.g., methanol 212) is often used in crystallization 150 but is not necessarily used in crystallization 220.

Alternatively or additionally, crystallization 150 optionally includes cooling from 55 to 25° C.

Alternatively or additionally, crystallization 220 optionally includes cooling from 55 to 35° C.

Alternatively or additionally, crystallization 220 and/or crystallization 150 often use an evaporative crystallizer with forced circulation.

Alternatively or additionally, crystallization 150 and crystallization 220 may each independently employ filtration (e.g., vacuum filtration) and/or centrifugation to separate the resultant crystals.

Optionally, a crystal habit modifier and/or L-methionine seed crystals are added to crystallization 150 and/or 220. An exemplary crystal habit modifier is polyoxyethylene sorbitan monolaurate (commercially available as TWEEN 20).

In some embodiments, crystallization 220 is conducted in the presence of an organic solvent, for example methanol and/or ethanol.

In some embodiments, mother liquor 200 is concentrated prior to second crystallization 220, optionally to a methionine concentration of about 150 g/l. In some embodiments, the solution is not clear at this concentration of methionine.

In some embodiments, crystallization 150 is conducted in the presence of a solvent (e.g., methanol 212), mother liquor 200 is evaporated (e.g., distillation 210) to recover the solvent (methanol 212) prior to crystallization 220. Optionally, the recovered solvent is reused in crystallization 150.

In some embodiments, second crop crystals 232 are dissolved 240 to form a solution 250 and combined with processed liquor 1020 before crystallizing 150. Optionally processed liquor 1020 is treated before combining. Optionally, impurities in processed liquor 1020 are removed as part of the treatment e.g., by filtration and/or active carbon treatment 130.

FIG. 3 is a schematic representation of a method for recovery of additional L-Methionine from mother liquor 200 indicated generally as 201. According to depicted exemplary method 201, mother liquor 200 is distilled 210 to recover methanol 212 which is optionally recycled to crystallization 150 of method 100. Methods 100 and 201 together are an exemplary embodiment of method 1000.

In the depicted exemplary embodiment, distillation 210 increases the concentration of L-methionine in the liquor so that secondary crystallization 220 of L-methionine occurs. Optionally, cooling during secondary crystallization 220 contributes to the crystallization process.

Secondary separation 230 (e.g., by centrifugation and/or filtration) produces a second crop of L-methionine crystals 232 and a "purged mother liquor" 300. In some embodiments, liquor 300 serves as a residual liquor.

In some embodiments, forming a residual liquor comprising free acetic acid includes contacting with a strong acid (e.g., sulfuric acid).

In some embodiments, forming a residual liquor comprising free acetic acid comprises at least one of contacting with $CO_2$ under pressure and contacting with a cation-exchanger that is at least partially in free acid form.

Optionally, crystals 232 are dissolved 240 to produce dissolved secondary crystals 250. In some exemplary embodiments of the invention, dissolved secondary crystals 250 are added to processed liquor 1020 prior to activated carbon treatment and/or filtration 130.

Figure 4:
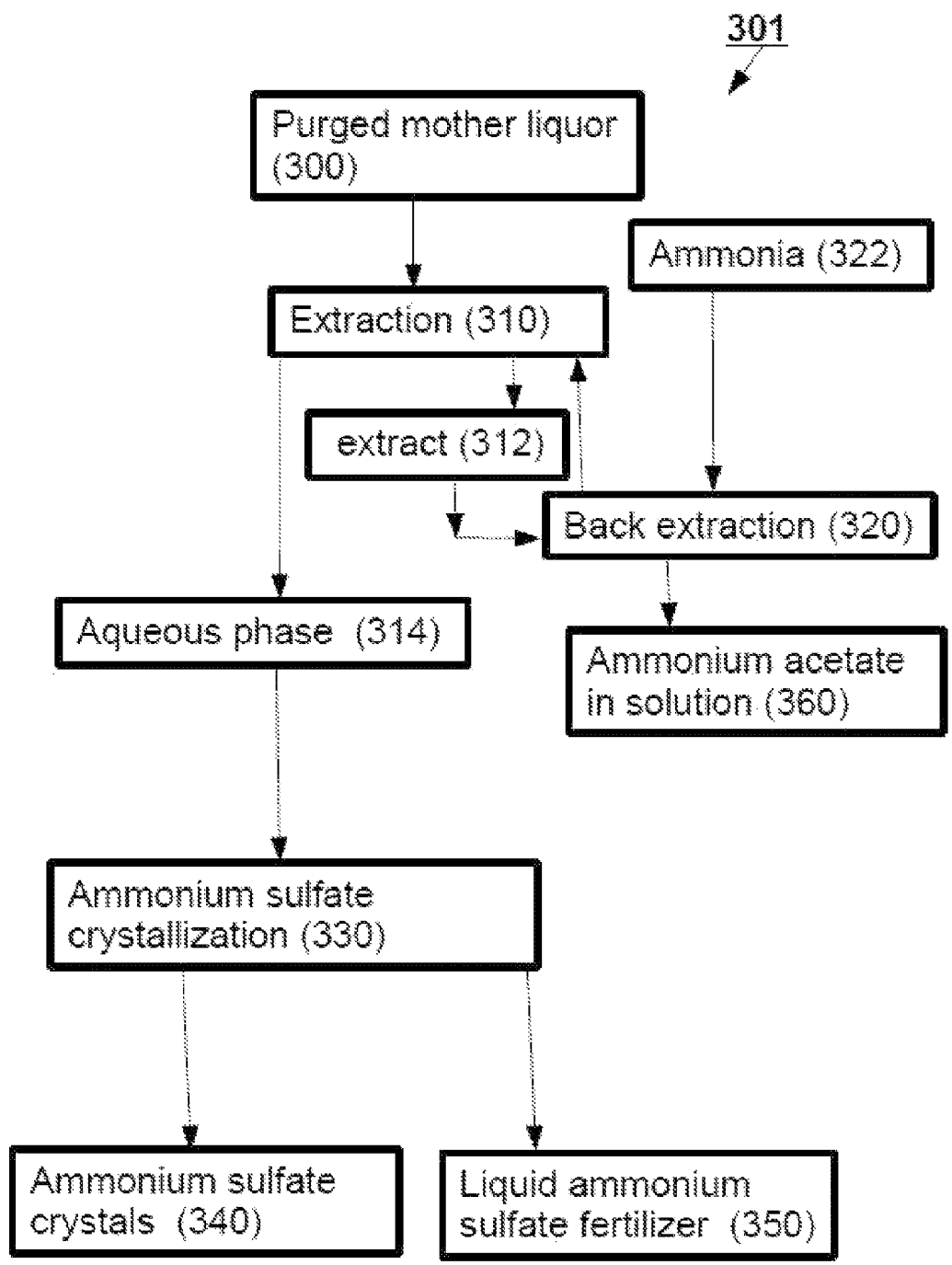

FIG. 4 is a schematic representation of an exemplary method for recovery of byproducts from a residual liquor indicated generally as 301. In the depicted exemplary embodiment, purged mother liquor 300 serves as a residual liquor. In the depicted exemplary method, purged mother liquor 300 is extracted 310 with an extractant including an organic solvent to produce an extract 312 containing the solvent and an aqueous phase 314.

In some embodiments, the pH of extract 312 and/or purged mother liquor 300 is adjusted to ≤4.5; ≤4.3; ≤4.1, or even ≤3.9. Optionally, this adjustment is made with sulfuric acid.

Alternatively or additionally, in some embodiments, a concentration of ammonium sulfate and/or a temperature of acidulated liquor 620 (FIG. 6) are adjusted to avoid ammonium sulfate crystallization during extraction. In some embodiments, this adjustment is made in consideration of water co-extracted with the acetic acid. Optionally ammonium sulfate concentration in acidulated liquor 620 is in the range between 12 wt % and 25 wt % and/or the extraction temperature is between 30 and 70° C.; optionally between 40 and 60° C.; optionally between 45 and 55° C.

According to various exemplary embodiments of the invention, extract 312 is manipulated to recover acetate in various ways. In the depicted embodiment, the manipulation includes back extraction 320 with ammonia 322 to produce ammonium acetate 360 in solution. Back extraction 320 also regenerates the extractant which can be recycled to extraction 310. In some exemplary embodiments of the invention, the solvent includes isobutyl acetate (IBA).

Figure 5:
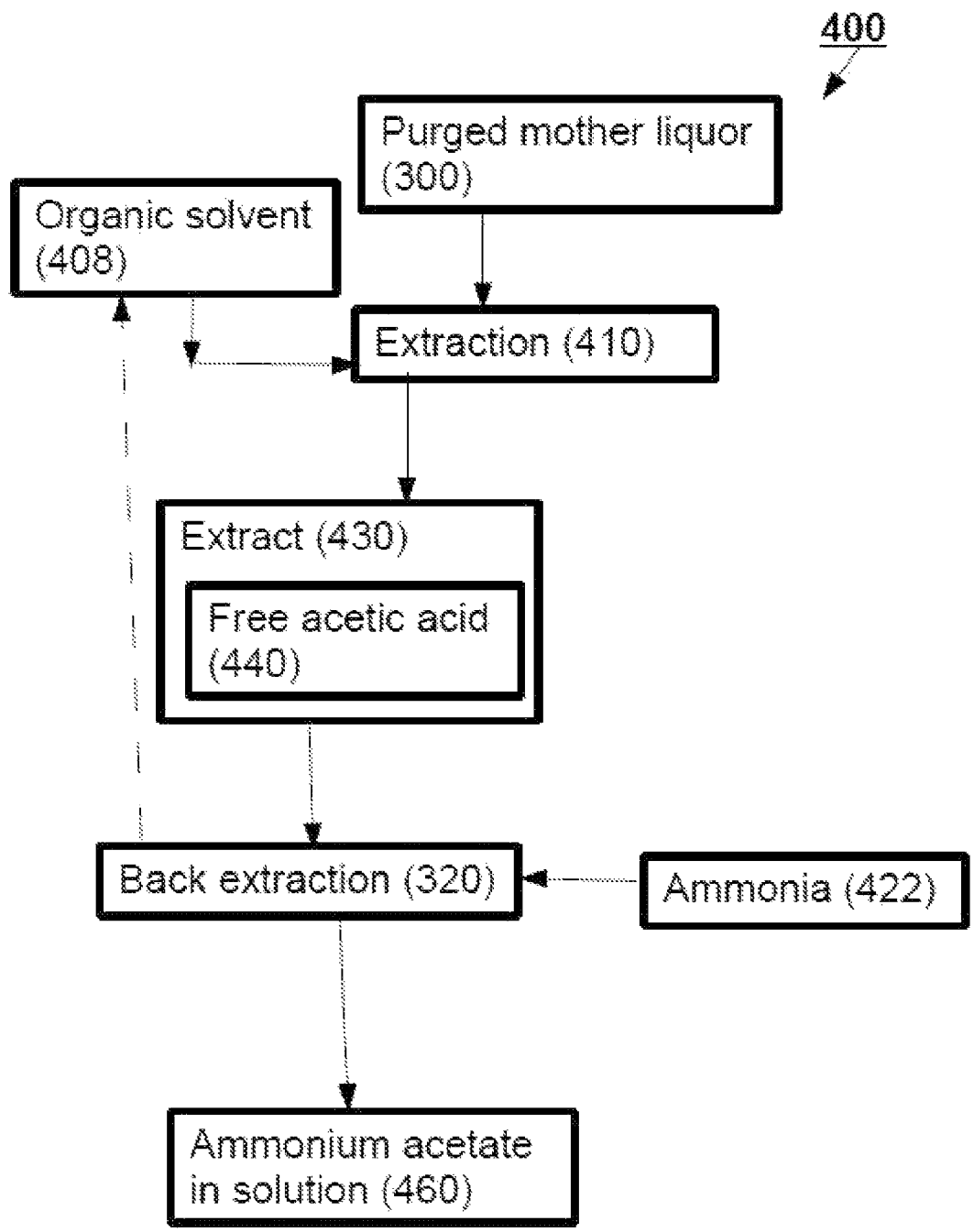
FIG. 5 is a schematic representation of a process for recovering acetic acid and/or acetate according to some exemplary embodiments of the invention.

In some embodiments, the extractant containing solvent 408 (FIG. 5) is recycled from a previous operation (e.g., back-extraction 320). Optionally, this recycling includes one or more washes with water and/or an aqueous solution (e.g., an alkaline solution) before re-use extraction 410 (FIG. 5).

Alternatively or additionally, in some embodiments, extraction 410 is conducted in a counter-current mode. Optionally, the extraction has 1, 2, 3 4 or even 5 or more stages.

In the depicted embodiment, aqueous phase 314 contains ammonium sulfate. Optionally, crystallization 330 precipitates a portion of the ammonium sulfate as crystals 340 which can be separated from the residual liquid ammonium sulfate fertilizer 350. Alternatively or additionally, ammonium sulfate crystals 340 can be used as a fertilizer ingredient.

In some embodiments, yield of ammonium sulfate crystals 340 is at least 40, 45, 50, 55 or even 60% or more.

In some embodiments, yield of ammonium acetate 360 is at least 85, 90, 93 or even 96% or more.

In some embodiments, purity of ammonium sulfate crystals 340 is at least 85, 87, 89 or even 92% or more In some embodiments, purity of ammonium acetate 360 is at least 95, 96, 97 or even 98% or more.

In some embodiments, ammonium sulfate crystallization 330 includes heating. Optionally, this heating results in separation of residual acetic acid in the vapor phase. Optionally, this residual acetic acid is condensed and concentrated, e.g., by reverse osmosis. Alternatively or additionally, heating causes evaporation of the dissolved/entrained solvent.

Referring now to FIG. 5, in some embodiments, recovering 1050 (FIG. 1) includes forming a residual liquor (depicted here as purged mother liquor 300) containing free acetic acid and separating the free acetic acid. In the depicted exemplary embodiment, separation is via extraction 410 with an extractant including an organic solvent 408 to form an extract 430 with free acetic acid 440.

Optionally, back extraction 320 with ammonia 422 can produce ammonium acetate 460 in solution (example of acetate 1052) and regenerate the extractant containing organic solvent 408.

Figure 6:
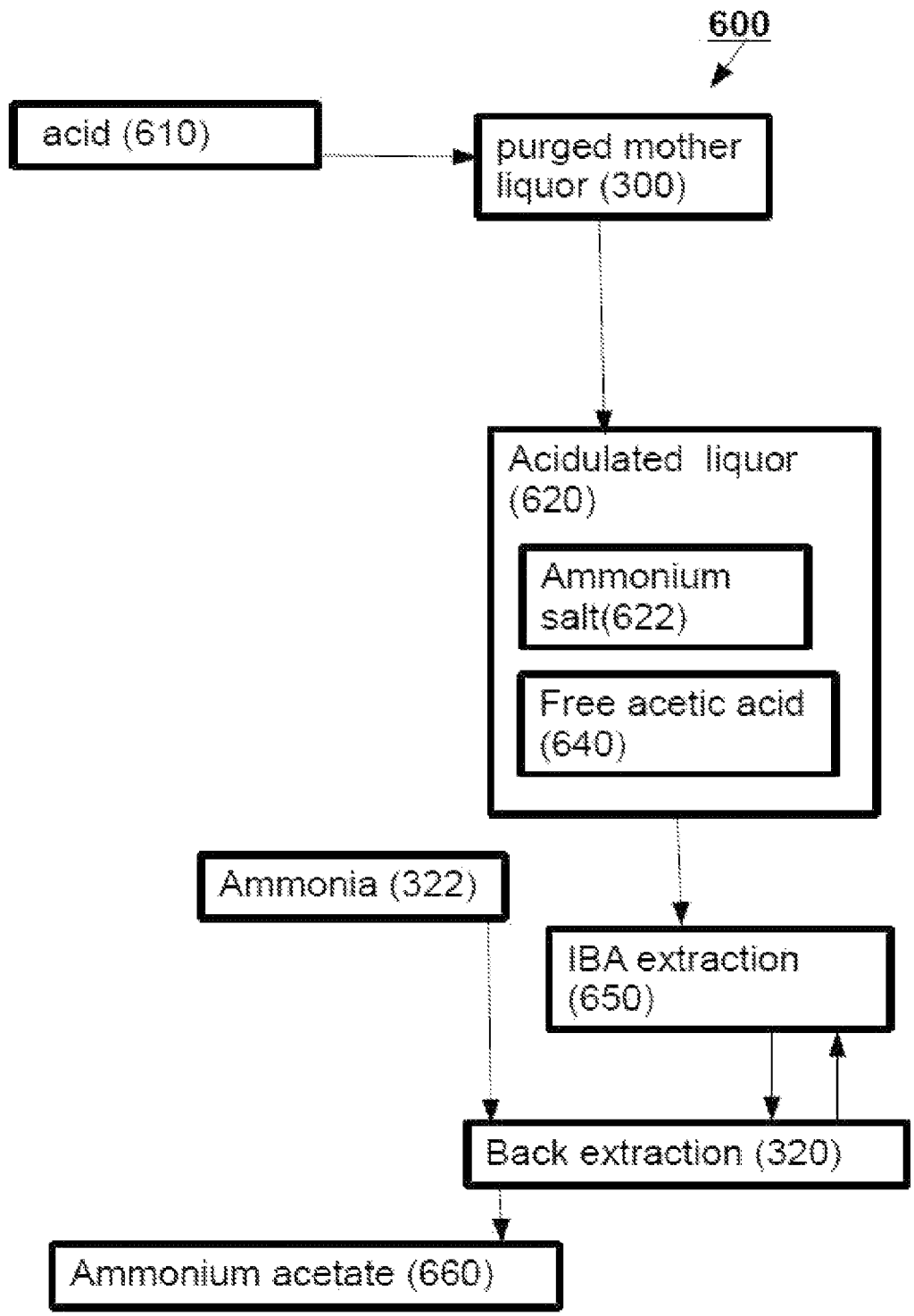
FIG. 6 is a schematic representation of a process for recovering ammonium acetate according to some exemplary embodiments of the invention.

Referring now to FIG. 6, in some exemplary embodiments of the invention, forming free acetic acid includes contacting the liquor (purged mother liquor 300 is depicted) with a strong acid 610 (e.g., sulfuric acid) to form an acidulated liquor 620. The strong acid can be any mineral or organic acid with $pKa \leq 4$.

In some embodiments, acid 610 is concentrated sulfuric acid, and addition to liquor 300 generates heat. Optionally, the temperature of acidulated liquor approaches a desired temperature for extraction 650, or even reaches the desired temperature.

In some embodiments, acidulated liquor 620 has a pH of 3 to 5; optional 3.5 to 4.5 optionally about 4.0. Optionally, acid 610 is added in a stoichiometrically equivalent, or greater, amount relative the amount of ammonium in liquor 300. Optionally, the stoichiometric excess is greater than 1, 3, 5, 8 or even 10% or more. If liquor 300 contains buffering agents, even greater amounts of acid 610 may be needed to reach a desired pH.

In some exemplary embodiments of the invention, a residual liquor to be acidulated (e.g., 300) is contacted with an acidic cation exchanger, to exchange cations in the liquor for protons (not depicted). According to these embodiments, this contacting contributes to acidulation of the solution.

Alternatively, an acidic cation exchanger is contacted with the residual liquor (e.g., 200) to be acidulated, thereby adsorbing ammonium ions. The acidulated residual liquor is treated for the removal of the acid (acetic or succinic), such as by extraction or adsorption on a thermally stable free base anion. After separation of the acid, methionine is crystallized out, dissolved and sent back to crystallization, and the ammonium carrying cation exchanger is regenerated with sulfuric acid to form a concentrated ammonium sulfate solution.

Alternatively or additionally, methionine is crystallized from a solution of essentially salt free solution. In some exemplary embodiments of the invention, a lower solute level prior to crystallization contributes to an increased yield. In some exemplary embodiments of the invention, ammonium sulfate solution is formed in a rather concentrated and pure form. Possibly it is used as such with no need for crystallization.

Optionally, forming the residual liquor including free acetic acid includes contacting with $CO_2$ under pressure. According to various exemplary embodiments of the invention the pressure of the carbon dioxide can be 3, 5, 7 or 10 bar or intermediate or greater pressures.

Optionally, forming residual liquor comprising free acetic and separating free acetic acid are conducted simultaneously. For example, acidulation with a strong acid or pressurized $CO_2$ and contacting with an extractant are conducted simultaneously in some embodiments. Alternatively or additionally, in some embodiments, partial acidulation is conducted first, followed by extraction and more acid is added during extraction.

Reference to separating free acetic acid indicates that it is free acetic acid while applying the separation means (e.g., distillation and/or extraction), but not necessarily that the recovered acetate is free acetic acid, e.g., as in extraction of free acetic acid and converting the free acid into a product while in the extractant.

Optionally, separating free acetic acid involves multiple steps, for example, distilling free acetic acid to form vapors containing free acetic acid, condensing the vapors to a solution containing the acetic acid and, optionally, further treating that solution, for example, extracting acetic acid out of it.

In some exemplary embodiments of the invention, recovering comprises distilling free acetic acid from the residual liquor. Optionally, distillation forms a condensate comprising free acetic acid.

In some exemplary embodiments, acidulated mother liquor has a pH value between 3.5 and 4.5, and optionally has a pH 4.0 In some exemplary embodiments, the distillated condensate has acetate contents of 10, 12, 14, 16 or even 18% or more.

Exemplary Acidulation Method

FIG. 6 is a simplified flow diagram of an exemplary liquor acidulation method indicated generally as 600. In depicted exemplary method 600, an acid 610 (e.g., sulfuric acid) is used to acidulate a residual liquor (purged mother liquor 300 is depicted as an example) to form acidulated residual liquor 620. In other exemplary embodiments of the invention, mother liquor 200 can serve as the residual liquor. In some embodiments, method 600 is performed on mother liquor 200 followed by performing method 201 to produce crystals 232.

In the depicted embodiment, acidulated liquor 620 includes ammonium salt 622 and free acetic acid 640. In the depicted exemplary embodiment, IBA (isobutyl acetate) extraction 650 is followed by back extraction 320 with ammonia 322. This back extraction converts free acetic acid 640 into recovered ammonium acetate 660.

Optionally, method 600 includes crystallizing at least a fraction of a salt of acid 610 from liquor 620 (not depicted in the figure). For example, if acid 610 is sulfuric acid, ammonium salt 622 is ammonium sulfate. Crystallization of ammonium sulfate is described in the context of FIG. 4.

Referring again to FIG. 5, in some embodiments, the method includes contacting extract 430 with water. Optionally, this contacting extracts acetic acid 440 into the water and re-generates the extractant containing organic solvent 408. Optionally, the acetic acid concentration can be increased by removing water. Water removal can be, for example, by distillation, evaporation and/or reverse osmosis.

In some exemplary embodiments of the invention, the method includes contacting extract 430 with an anti-solvent and evaporation.

In some exemplary embodiments of the invention, the method includes contacting a liquor comprising free acetic acid (depicted as acidulated purged mother liquor 620) with an extractant (depicted as IBA extraction 650) to form an acetic acid-comprising extract and an acetic acid depleted residual liquor.

According to various exemplary embodiments of the invention the "liquor comprising free acetic acid" can be residual liquor comprising free acetic acid or condensate liquor comprising free acetic acid.

Optionally, the method includes separating the extract from the liquor to form separated extract and separated acetic acid depleted residual liquor.

In some embodiments, the contacting with the extractant results in selective extraction. Optionally the acetic acid/strong acid selectivity is at least 50, at least 100, at least 200 or even at least 500.

Exemplary Acetic Acid Recovery

In some embodiments, an extractant comprising at least one organic solvent is used to extract acetic acid from a liquor. Suitable organic solvents for use in such an extractant include, but are not limited to alcohols, aldehydes, ketones, esters (e.g., C4-C8 esters) and amines (e.g., $C \geq 20$ atoms). In some embodiments, the acetate esters includes a C4 ester e.g., butyl acetate and/or isobutyl acetate.

In some embodiments, extraction is with one or more acetate esters. Optionally, the esters include a butyl acetate, optionally isobutyl acetate (IBA). In some embodiments, the IBA includes isobutanol resulting from partial hydrolysis.

Referring again to FIG. 4, in some embodiments, extraction 310 is more than 90, 92, 94, 96, or even more than 98% efficient at extracting acetic acid from purged mother liquor 300 (i.e., less than 10% of available acetate remains in aqueous phase 314).

In some embodiments, extraction 310 is conducted in a countercurrent mode, optionally using one or more apparatus. Suitable apparatus include, but are not limited to mixer-settlers, columns, pulsating columns and centrifugal contactors.

Optionally, extraction 310 is conducted in 3 to 15, optionally 4-14 stages.

In some embodiments, extraction 310 uses 2, 3, 4, 5 or even 6 or more weight units of extractant per weight unit of (aqueous) purged mother liquor.

Alternatively or additionally, a ratio of acetic acid 440 (FIG. 5) to water in extract 430 is between 15 and 40, optionally between 20 and 30.

Alternatively or additionally, an acetic/sulfuric selectivity of solvent 408 (FIG. 5) in the extractant is 50, optionally 100, optionally 200, optionally 500 or more.

Alternatively or additionally, an acetic/water selectivity of solvent 408 in the extractant is at least 10, optionally at least 20, optionally at least 30, optionally at least 40.

Exemplary Solvent for Use in an Extractant

In some exemplary embodiments of the invention, IBA is used as solvent 408, or a portion of a solvent mixture in the extractant. In some embodiments, the extractant is contacted with an acidic solution (e.g., acidulated purged mother liquor; APML).

That acidity and a temperature higher than ambient each contribute to hydrolysis of IBA. Testing at the conditions of extraction has shown that hydrolysis occurs at acceptable levels. Hydrolysis forms acetic acid that combines with the extracted acetic acid and is separated from the extract along with it as well as isobutanol (IB). The concentration of IB reaches a steady state level in the extractant due to some losses balanced by makeup of IBA and/or reaction with extracted acetic acid to reform IBA.

In some embodiments, the recycled extractant contains a steady state level of IB. According to some embodiments the level of IB is 0.1 to 20%, optionally 0.2-15%, optionally 0.3 to 10%. Exact concentration may vary with pH of the acidulated purged mother liquor and/or the extraction temperature and/or ammonium sulfate concentration and/or other parameters. In some embodiments, IB content in the IBA increases extraction efficiency.

In some embodiments, recovering 1050 of acetate 1052 (FIG. 1) includes recovery of acetate from the acetic acid-comprising extract to form recovered acetate.

FIG. 6 depicts one example of this strategy. IBA extraction 650 to produce ammonium acetate 660 is an example of recovery 1050. Although PML 300 is depicted, this could be done on any residual liquor.

According to various exemplary embodiments of the invention the recovered acetate can include acetic acid and/or a salt of acetic acid and/or an ester of acetic acid.

Alternatively or additionally, recovering may include contacting separated extract with water to form back-extracted acetic acid and/or contacting the extract with a base solution (e.g., ammonia 322) to form a salt of acetic acid and that base (e.g., ammonium acetate 660) and/or contacting the extract with an anti-solvent to form a solution of acetic acid and/or evaporation of the extract or a fraction of it to form a solution of acetic acid (where the extractant is more volatile than acetic acid) and/or evaporating acetic acid from the extract (where the extractant is less volatile than acetic acid); and/or contacting the extract with an alcohol and inducing a reaction between the alcohol and the extracted acetic acid to form the corresponding ester, followed by separating the ester from the extractant.

According to various exemplary embodiments of the invention back extraction 320 can be with a base including one or more of bases of alkaline, bases of alkaline earth metals and bases of ammonia. In this context, the term "bases" includes oxides, hydroxides, bicarbonates and carbonates.

In some embodiments, extraction 650 occurs in a contacting apparatus. Exemplary contacting apparatus include mixer-settlers, columns, pulsating columns and centrifugal contactors. Optionally, contacting is with water or an aqueous solution.

Optionally, this contacting occurs in a multi-stage counter-current mode. In some embodiments, a ratio of water/extract w/w for this contacting is one unit weight of extract to between 2 to 6 unit weight of water. Alternatively or additionally, this contacting occurs in 3 to 15, optionally 4 to 14 stages. Alternatively or additionally, the yield of back extraction 320 is at least 90, at least 93, at least 95, at least 97, or even 99% or more. Alternatively or additionally, the concentration of formed aqueous acetic acid solution is at least 10, optionally at least 12, optionally at least 14, optionally at least 18%.

In some embodiments, the contacting is a single-stage contacting with a base solution. Optionally, this contacting occurs in a mixer-settler or a centrifugal contactor.

In some embodiments, back extraction 320 is with an anti-solvent. As used in this specification and the accompanying claims the term an "anti-solvent" is a solvent that is a good solvent for the extractant and a poor solvent for acetic acid 440.

In some embodiments, use of an anti-solvent in back extraction 320 produces extractant solution in the anti-solvent and a separate aqueous phase containing separated acetic acid 440. In order to regenerate the extractant containing organic solvent 408, the anti-solvent must be separated from solvent 408. Optionally, this separation involves distillation of the more volatile component.

According to various exemplary embodiments of the invention the anti-solvent is selected to be more hydrophobic than the extractant including solvent 408, e.g., as determined by solubility parameter of Log P. According to an embodiment, while being more hydrophobic than the extractant, the anti-solvent is more polar than octane.

Some embodiments of the invention include contacting (back extraction 320; FIG. 5) an acetic acid-comprising extract 430 with a base (e.g., ammonia 422) to form recovered acetate salt (ammonium acetate 460) of the base.

Optionally, the ammonia concentration in back extraction 320 reagent is 15 to 25%, optionally 19 to 23%, optionally about 21%. In some embodiments, the weight percentage of ammonium acetate in back extraction 320 is 40%, 42%, 46% or even 48% or more. Optionally, solution 460 contains 70%, 75% or even 80% or more ammonium acetate. Alternatively or additionally, solution 460 contains 860 g/l or more ammonium acetate after concentration of the Ammonium acetate. The ammonium acetate concentration is optionally about 520 g/l prior to the concentrating.

According to various exemplary embodiments of the invention ammonia 422 can be supplied as a solution, a gas or a combination thereof.

In some exemplary embodiments of the invention, back-extracting 320 is with a base, e.g., ammonia 422 or another base as listed hereinabove. According to various exemplary embodiments of the invention the base is solid (e.g., lime), gaseous (e.g., ammonia 422) or in an aqueous solution.

According to various exemplary embodiments of the invention, the amount of base is selected to be between 0.97 and 1.2, optionally between 0.98 and 1.15, optionally between 0.99 and 1.1, and optionally between 1 and 1.05 equivalents per equivalent of acetic acid in extract 430.

In some embodiments, contacting is with an aqueous ammonia solution, the concentration of which is adjusted so that a concentration of ammonium acetate in solution 460 is at least 30, optionally 40, optionally 50% w/w or more.

Alternatively, in some embodiments, contacting is with a solution comprising ammonia and ammonium acetate. Optionally, the solution is characterized by and NH3/ammonium acetate ratio of 0.02 to 50, optionally 0.04 to 25, optionally 0.05 to 10, optionally 0.08 to 5, optionally 0.1 to 2. According to these embodiments, addition of ammonium acetate allows conducting back-extraction at a lower pH and therefore minimizes extractant degradation. The amount of ammonia is determined by the stoichiometry requirements above, and the concentration of NH3 and ammonium acetate are adjusted to reach a desired ammonium acetate concentration.

In some embodiments, the aqueous product of the back-extraction is split into at least two streams. One stream is the recovered acetic acid, and a second stream is combined with ammonia to reform the Ammonium acetate/NH3 solution for recycling to back-extraction. Optionally, concentration of the aqueous product of the back-extraction is as defined above. Alternatively or additionally, a pH of the aqueous product of the back-extraction is in the range 6 to 9 optionally 7 to 8.

According to an embodiment, the amount of ammonia in the back-extracting solution is in excess so that the formed ammonium acetate contains free ammonia. According to an embodiment, that free ammonia is distilled out of the solution (and reused in back-extraction).

According to an embodiment, the ammonium acetate solution formed on back-extraction is further concentrated >40, >50, >60, >70% or more. According to an embodiment the solution has excess ammonia and that excess ammonia is removed during that concentration.

According to an embodiment, the ammonium acetate solution has some dissolved or entrained IBA and/or IB from the extractant. According to an embodiment, this solvent is distilled out, at least partially, during the concentration of the ammonium acetate solution.

Referring again to FIG. 5: a temperature at which back extraction 320 occurs is determined by the temperature of incoming extract 430 (optionally warm from extraction), of the ammonia solution 422 or ammonia with ammonium acetate solution as described above and by some heat generated in the back-extraction. Typically, there is no need for adjustment, but some cooling might be desired in order to limit the temperature to about ambient temperature.

In some embodiments, extract 430 is washed with an aqueous solution containing a small amount of base prior to back-extraction 320 of the acetic acid in order to remove impurities. Due to the selectivity of the extractant, the impurities are removed with essentially no loss of acetic acid.

Optionally, co-extracted sulfuric acid in extract 430 is removed by washing with a base in an amount equivalent to the amount of sulfuric acid in the extract.

In some embodiments, the process includes acetic acid and/or ammonia recovery from ammonium acetate solution 460. Optionally, this recovery includes heat treatment.

Referring now to FIG. 6, IBA used in extraction 650 may react slightly at the conditions of back-extraction 320. In such a reaction, Isobutanol (IB) and/or acetamide are formed.

In some embodiments, conditions in back-extraction 320 are maintained so as to minimize reaction of IBA. For example, temperature is optionally maintained not much higher than ambient, but working below ambient is typically not required. Alternatively or additionally, back-extraction with NH3+ ammonium acetate solution (as described above) while maintaining that solution at pH of less than 11, optionally less than 10.5, optionally less than 10 can contribute to a reduction in IBA reaction.

Testing of back-extraction 320 has shown that in these conditions solvent degradation is small (see Example 5).

In some embodiments, IB formed during back-extraction 320 degradation combines with that of hydrolysis during extraction and together reaches a steady state level as discussed above.

In those embodiments in which acetamide forms during degradation, the acetamide is washed out into ammonium acetate solution 660.

In some embodiments, the residual liquor includes a salt of a strong mineral acid with a water solubility of less than 5% wt. According to various exemplary embodiments of the invention the salt with water solubility <5% is calcium sulfate or calcium phosphate.

According to various exemplary embodiments of the invention, methyl mercaptan is introduced to enzymatic processing 120 as a calcium or magnesium salt, or as a free acid and the pH is adjusted by a calcium or magnesium base. Optionally, the resultant solution (containing methionine and acetate source) is acidulated to pH 5 for cell separation, carbon treatment or both. Optionally, that pH adjustment is done with acetic acid, rather than sulfuric acid.

In those cases where pH adjustment is done with acetic acid the PML 300 formed after methionine crystallization 220 contains mainly calcium acetate as the acetate source. According to an embodiment, that PML is then acidulated (see 610), at least partially, with sulfuric acid (or phosphoric acid), whereby gypsum (or calcium phosphate) is formed. According to an embodiment, these low-solubility salts are separated (e.g., by filtration and/or centrifugation), leaving a solution comprising acetic acid in free acid form (acidulated liquor 620 with free acetic acid 640). Optionally, free acetic acid 640 is then separated according to any of the previously described methods.

According to an embodiment the low solubility salt is formed as a result of ammonia recovery by means of a calcium base, as described below.

In some embodiments, the residual liquor includes an ammonium source, and the method includes recovering at least a portion of the ammonium source from the residual liquor as recovered ammonia.

Optionally, the residual liquor comprises ammonium acetate. According to various exemplary embodiments of the invention, ammonium in the ammonium source and in the recovered ammonium are each independently selected from an ammonium salt and free-base ammonia.

Figure 7:
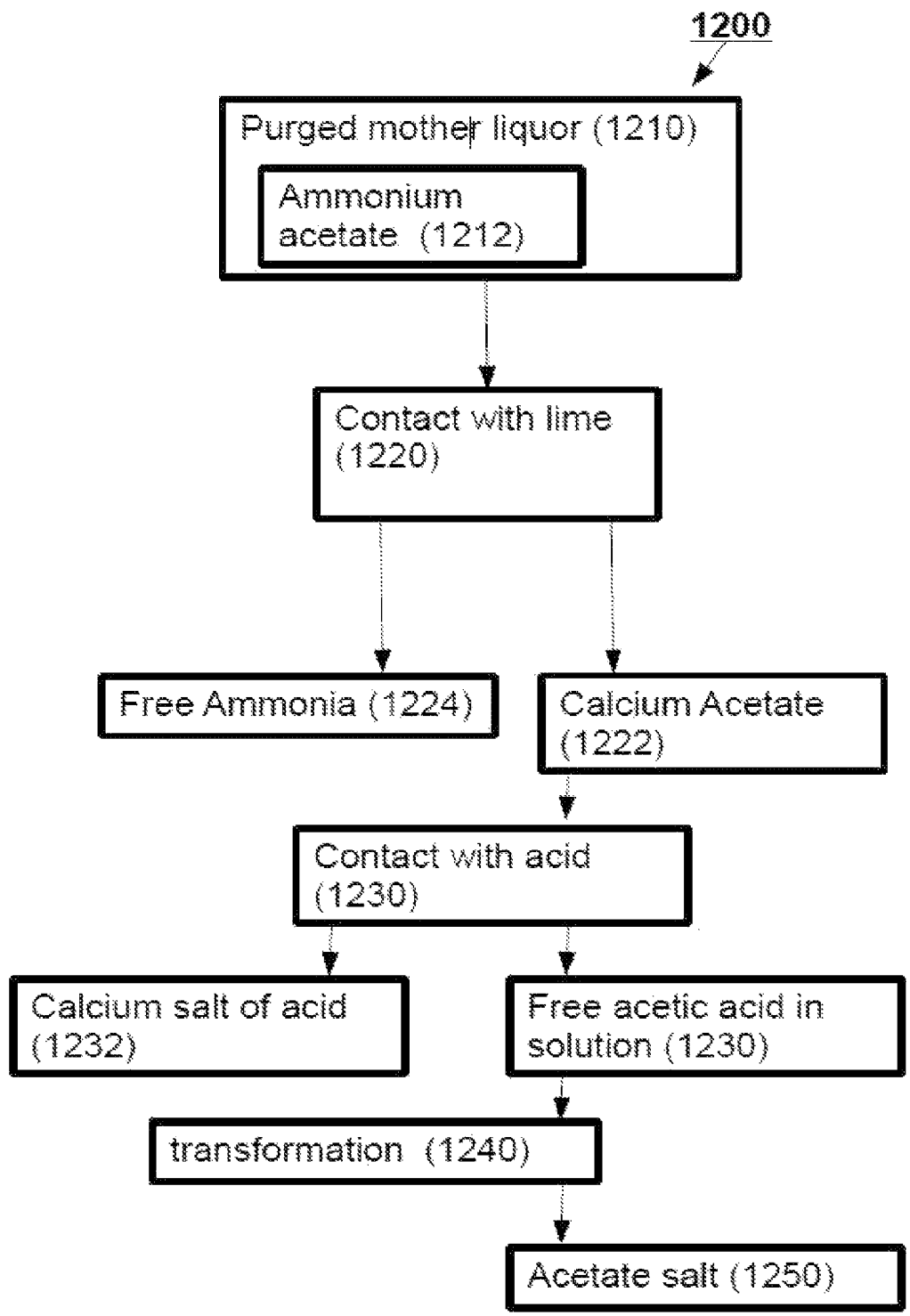
FIG. 7 is a schematic representation of a process for recovering calcium salts and acetate salts according to some exemplary embodiments of the invention.

Referring now to FIG. 7, in some embodiments, the method includes contacting the residual liquor (e.g., purged mother liquor 1210) with a calcium base (e.g., lime 1220) to form free-base ammonia and a calcium salt (e.g., calcium acetate 1222) and separating free-base ammonia to form recovered ammonium 1224 and separated ammonia-depleted residual liquor including a calcium salt.

In some embodiments, this method further includes adding a strong acid 1230 to the separated ammonia-depleted residual liquor to form a calcium salt 1232 of the acid and a residual liquor comprising free acetic acid 1230 and optionally separating (e.g., by evaporation) at least a fraction of the acetic acid to form a residue solution depleted of ammonia and acetic acid. According to various embodiments, separation of free acetic acid uses methods as described above, including evaporation and solvent extraction.

In the depicted exemplary embodiment, production of acetic acid 1230 is an example of recovery 1050 of acetate 1052. Transformation 1240 to acetate 1250 is depicted to emphasize this point although the process concludes with free acetic acid in solution 1230 in many embodiments.

In some embodiments, the residual liquor comprises ammonium acetate and the recovering at least a portion of ammonium includes distilling ammonia and optionally a portion of the acetic acid from the residual liquor to form separated ammonium (recovered ammonium) and ammonia-depleted residual liquor.

Optionally, the residual liquor comprises ammonium acetate and said recovering at least a portion of the ammonium includes contacting the residual liquor with pressurized $CO_2$ and/or with an extractant. According to various exemplary embodiments of the invention contacting with pressurized $CO_2$ and/or extractant results in the formation of ammonium carbonate and/or ammonium bicarbonate and an acetic acid-loaded extract. According to an embodiment, the aqueous solution with the ammonium carbonate/bicarbonate is used as recovered ammonium. In others ammonium carbonate/bicarbonate is crystallized and the crystals are used as the ammonium source.

In those embodiments in which the gypsum formed is of sufficiently high quality for applications such as gypsum board (or in cement), it could be a more attractive co-product than ammonium sulfate, considering the difference in prices between the bases and the fluctuations in fertilizer prices. The gypsum quality could be similar to that formed in the production of citric acid and of lactic acid.

Alternatively or additionally, it is possible that the purge after separation of the gypsum and the acetic acid could be economically sent to waste-water treatment. Optionally, after some pretreatment or purging of impurities, the purge after separation of the gypsum and the acetic acid can be used for diluting the enzymatic reaction system, saving thereby on evaporation costs.

Ammonium ion concentration in the feed to contacting with lime 1220 varies with the ammonium acetate concentration in purged mother liquor 1210.

According to various exemplary embodiments of the invention contacting with lime 1220 includes contacting one or more of calcium oxide, calcium hydroxide, calcium carbonate and calcium bicarbonate.

In some embodiments, the amount of lime used at contacting 1220 is equivalent to the amount of ammonium in PML 1210 or 1, 2, 5, or 10% higher on a molar basis.

In some embodiments, free ammonia 1224 is used as the recovered ammonium. In some embodiments, free ammonia 1224 is condensed to form an ammonia solution which is used as the recovered ammonium.

In some embodiments, at least a fraction of the recovered ammonium is used in production of a fermentation product. According to various exemplary embodiments of the invention recovered ammonium provides a nitrogen source in fermentation. Optionally, the fermentation produces an amino acid (e.g., lysine or threonine or valine) or an amino acid precursor (e.g., OAHS or OSHS).

Alternatively or additionally, at least a fraction of the recovered ammonium is used in preparation of ammonia methyl mercaptan and/or to neutralize the medium of the enzymatic reaction (120) or for pH adjustment.

In some embodiments, the method includes: crystallizing an ammonium salt from the residual liquor to form a crystalline ammonium salt and separated ammonia-depleted residual liquor. Optionally, the ammonium salt includes one or more of ammonium acetate, ammonium carbonate and ammonium bicarbonate.

Additional Exemplary Method

Figure 9:
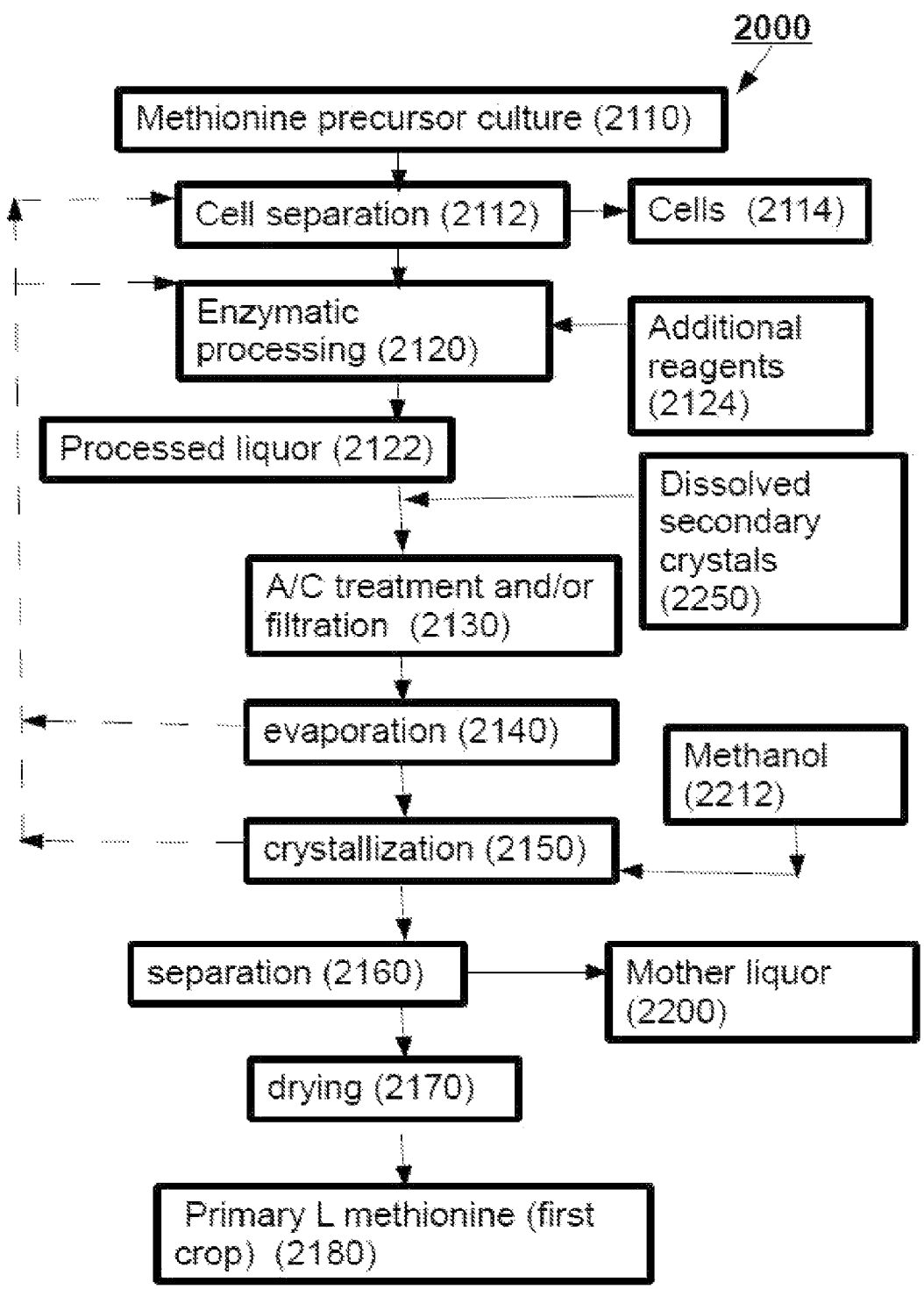
FIG. 9 is a schematic overview of a process for producing L-methionine according to some exemplary embodiments of the invention.

FIG. 9 is a simplified flow diagram of a method for producing methionine indicated generally as method 2000. Depicted exemplary method 2000 is similar to method 100 (FIG. 2) in many ways and items indicated by a reference numeral 2NNN correspond to items indicated by reference numeral NNN in FIG. 2.

Depicted exemplary method 2000 includes providing a fermentation liquor comprising an L-methionine precursor selected from the group consisting of O-acetylhomoserine and O-succinyl homoserine. Providing, in the depicted embodiment includes separating 2112 cells 2114 from a methionine precursor culture 2110.

Optionally, the fermentation liquor includes at least one impurity. According to various exemplary embodiments of the invention, at least one impurity includes amino acids and/or vitamins and/or minerals and/or ammonia and/or acetic acid and/or succinic acid and/or methyl mercaptan and/or enzymes.

Depicted exemplary method 2000 includes enzymatically processing 2120 the precursor to produce a processed liquor 2122 comprising L-methionine and an organic acid selected from the group consisting of acetic acid and succinic acid. Optionally, at least a portion of the at least one impurity remains in liquor 2122.

Depicted exemplary method 2000 includes modifying processed liquor 2122 to form a crystallizing feed and crystallizing 2150 L-methionine from the crystallizing feed to form crystalline L-methionine 2180 and an L-methionine-depleted mother liquor 2200.

According to various exemplary embodiments of the invention, modifying includes one or more of water removal (e.g., evaporation 2140), active carbon treatment 2130, addition of a solute (e.g., dissolved crystals 2250), pH adjustment, ion-exchange, membrane filtration 2130 and contacting with at least one water-soluble organic solvent (e.g., methanol 2212). Optionally, the water-soluble organic solvent is selected from the group consisting of C1-C4 alcohols and a combination thereof. In some embodiments, the water-soluble organic solvent includes methanol and/or ethanol.

In some embodiments, method 2000 includes separating 2160 crystalline L-methionine 2180 from mother liquor 2200.

According to various exemplary embodiments of the invention crystalline L-methionine 2180 is characterized by purity greater than 95%, 96, 97, 98.5 or even greater than 99%.

Alternatively or additionally, crystalline L-methionine 2180 is characterized by containing less than 1, 0.5, 0.25 or even less than 0.1% acetate source or succinate source by weight.

Alternatively or additionally, crystalline L-methionine 2180 is characterized by an OAHS or OSHS content greater than 1, 10, 20, 50 or even 100 PPM or intermediate or greater concentrations.

Alternatively or additionally, crystalline L-methionine 2180 is characterized by a content of at least one particular impurity greater than 1, 10, 20, 50 or even 100 PPM or intermediate or greater concentrations.

Alternatively or additionally, crystalline L-methionine 2180 is characterized by a content of less than 2, 1.5, 1, 0.5 or even 0.1% or intermediate or lower concentrations of D-methionine. Optionally, the crystals are substantially enantiomerically pure.

Alternatively or additionally, crystalline L-methionine 2180 is characterized by a carbon-14 to carbon-12 ratio of at least $2.0 \times 10^{-13}$.

Alternatively or additionally, crystalline L-methionine 2180 is characterized by a concentration of less than 0.8, 0.6, 04, 0.2 or even 0.1% organic acid or intermediate or lower concentrations.

In some exemplary embodiments of the invention, crystalline L-methionine 2180 is characterized by 2 or more of these characteristics.

In some exemplary embodiments of the invention, crystalline L-methionine 2180 is characterized by 3 or more of these characteristics.

In some exemplary embodiments of the invention, crystalline L-methionine 2180 is characterized by 4 or more of these characteristics.

In some exemplary embodiments of the invention, crystalline L-methionine 2180 is characterized by 5 or more of these characteristics.

Unless specified otherwise, organic acid indicates free acid form and/or salt form.

In some exemplary embodiments of the invention, modifying includes combining the reaction product stream with an L-methionine-comprising recycle stream 2250.

In some embodiments, at least 85% of the amount of L-methionine in reaction liquor 2122 is crystallized to crystalline L-methionine 2180.

In some embodiments, the method includes separating L-methionine from mother liquor 2200 to form L-methionine-comprising recycle stream (dissolved secondary crystals 2250) and a purged mother liquor stream. In some embodiments, separating L-methionine from mother liquor 2200 includes crystallization to form a second crystalline L-methionine and separating of the second crystalline L-methionine from the purged mother liquor. This process is analogous to that described hereinabove in the context of FIG. 3.

In some exemplary embodiments of the invention, the crystallizing feed comprises the L-methionine precursor at a concentration of at least 1, optionally at least 5, optionally at least 10 PPM.

Optionally, crystallizing from the mother liquor includes evaporative crystallizing.

According to various exemplary embodiments of the invention the crystallization conditions of both crystallizations and the composition of the second crystalline L-Methionine are as described hereinabove.

In some embodiments, crystallizing L-methionine from the crystallizing feed stream includes the use of at least one of a crystal habit modifier and/or L-methionine seed crystals. Optionally, the crystal habit modifier is polyoxyethylene sorbitan monolaurate (commercially available as TWEEN 20).

In some embodiments, the method includes recovering at least a portion of the organic acid from said mother liquor as recovered organic acid. Optionally, the method includes recovering at least a portion of the organic acid from the purged mother liquor as recovered organic acid.

In some exemplary embodiments of the invention, processing includes contact with an anion exchanger and at least a fraction of the organic acid is adsorbed on the anion exchanger. Optionally, the anion exchanger is optionally in the form of free base and/or carries methyl mercaptan anions.

In some exemplary embodiments of the invention, methyl mercaptan is introduced in its free acid form ($CH_3SH$) and acetic or succinic acid is generated in its free acid form. Use of methyl mercaptan in free acid form causes liberation of acid which can reduce the pH to a level incompatible with enzymatic processing 2120. In some embodiments, processing 2120 is conducted in the presence of an anion-exchanger which binds the liberated acid so that effects on pH are moderated. In some embodiments, methyl mercaptan in its free acid form is used with a precursor culture 2110 containing OSHS. In this case, the liberated acid is succinic acid which has a relatively low solubility in water. Optionally, precipitation of succinic acid limits pH drop.

Optionally, after separation of the acid-loaded resin, methionine is crystallized from the reaction solution, which is now low in mineral salt.

Alternatively or additionally, the acid-loaded anion exchanger is treated for regeneration and for the recovery of the acid or its product.

Optionally, the anion-exchanger is thermally stable (e.g., Reilex type) and acetic acid is recovered from it by distillation or by a reaction with an alcohol (e.g., ethanol) to form the corresponding ester (ethyl acetate).

In some exemplary embodiments of the invention, this strategy contributes to a reduction in consumption of ammonia and/or sulfuric acid. It follows that any costs related to production of ammonium sulfate (water distillation, crystallization and drying) are reduced to a corresponding degree.

Alternatively or additionally, methionine is crystallized from a solution of much lower total solutes. In some exemplary embodiments of the invention, a lower solute level prior to crystallization contributes to an increased yield and/or improved purity and/or a reduction in resources allocated to producing a second crop of methionine crystals.

In some exemplary embodiments of the invention, the methionine precursor is O-succinyl homoserine and the organic acid is succinic acid. According to these embodiments, processing is conducted in the presence of calcium ions. Reaction of succinic acid and calcium ions can cause precipitation of calcium succinate.

In some embodiments, methyl mercaptan is introduced in its calcium salt form into enzymatic reaction with OSHS. The liberated succinic acid precipitates out as calcium succinate, maintaining thereby the desired pH.

At the end of the reaction, the succinate salt can be separated prior to crystallization of methionine. Optionally, succinic acid is then liberated from its salt. Liberation can be, for example, by acidulation with sulfuric acid.

In some exemplary embodiments of the invention, lime is consumed instead of ammonia and gypsum is formed instead of ammonium sulfate.

In some embodiments, methionine is crystallized from a solution of much lower total solutes. In some exemplary embodiments of the invention, a lower solute level prior to crystallization contributes to an increased yield and/or improved purity and/or a reduction in resources allocated to producing a second crop of methionine crystals.

Additional Exemplary Method

Figure 10:
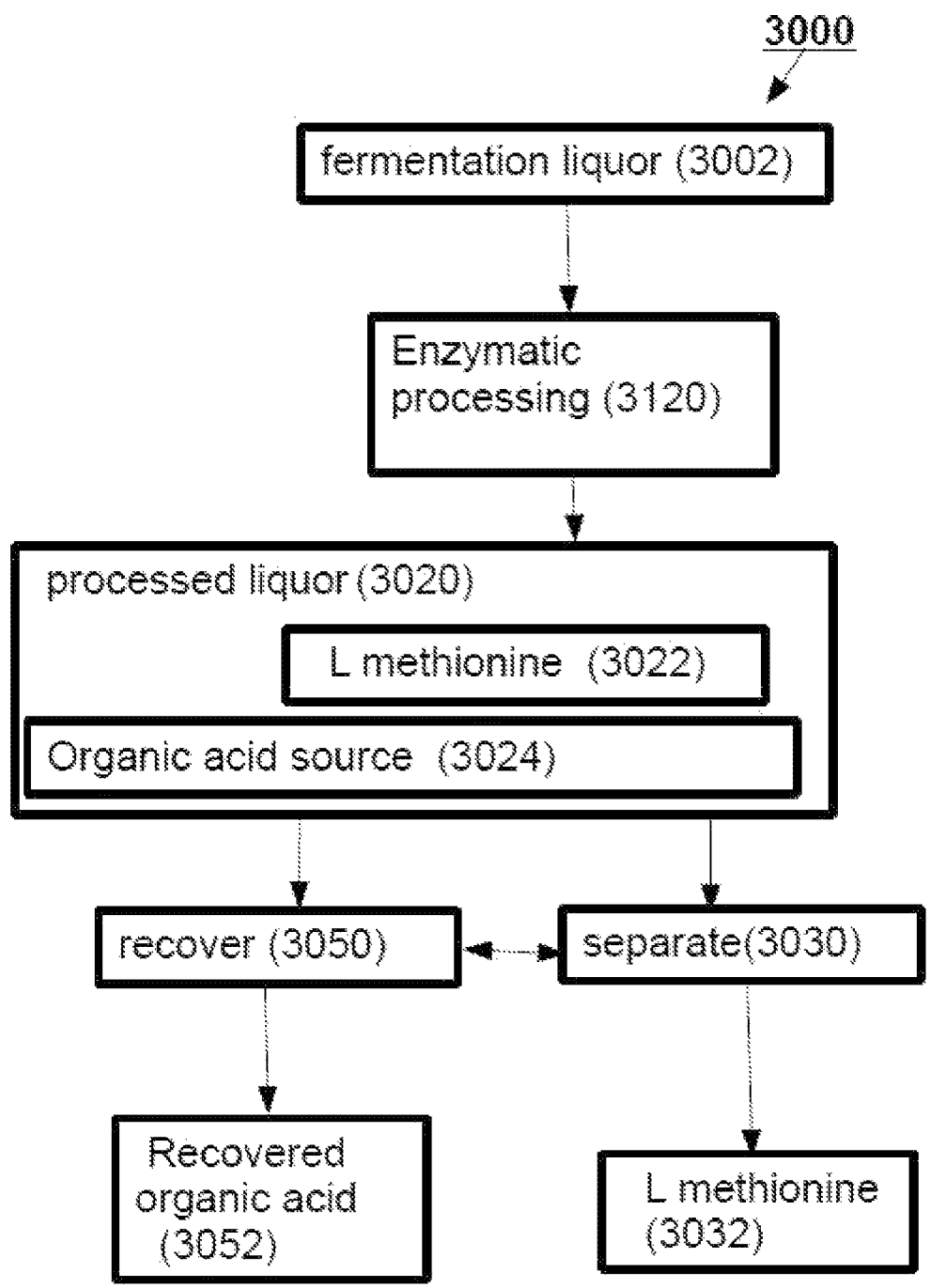
FIG. 10 is a schematic overview of a process for recovering organic acid during methionine purification according to some exemplary embodiments of the invention.

FIG. 10 is a schematic representation of a method for recovering an organic acid during production of methionine depicted generally as 3000. Depicted exemplary method 3000 includes enzymatically processing 3120 a fermentation liquor 3002 comprising an L-methionine precursor. According to various exemplary embodiments of the invention the precursor includes O-acetylhomoserine (OAHS) and/or O-succinyl homoserine (OSHS). Processing 3120 produces L-methionine 3022 and a source of an organic acid 3024. Source 3024 can include acetic acid and/or succinic acid depending upon the precursor in liquor 3002.

The depicted exemplary method includes separating 3030 at least a portion of L-methionine 3022 from at least a fraction of the source of organic acid 3024 to form separated L-methionine 3032 and a residual liquor comprising the source of organic acid 3024 and recovering 3050 at least a portion of the source of organic acid from the residual liquor as recovered organic acid 3052. Recovering 3050 and separating 3030 can be performed sequentially (in either order) or simultaneously.

In some embodiments, method 3000 includes using recovered organic acid 3052 as a reagent. In some embodiments, recovered organic acid 3052 is used in production of a fermentation product. Optionally, the fermentation product is selected from the group consisting of carboxylic acids and amino acids. Optionally, the amino acids include one or more of lysine, threonine, tryptophan, arginine, valine and methionine.

In some embodiments, recovered organic acid 3052 is used in the processing of a fermentation liquor.

In some embodiments, recovered organic acid 3052 is used as an ingredient in a fermentation medium.

In some exemplary embodiments of the invention, the L-methionine precursor is O-succinyl homoserine and the organic acid is succinic acid. According to many of these embodiments, recovering 3050 includes forming a residual liquor including free succinic acid and separating the free succinic acid (as recovered organic acid 3052).

Exemplary Compositions of Matter and Products Containing them

In some embodiments, there is provided a composition comprising L-methionine, characterized by at least one characteristic selected from the group consisting of:

(i) containing less than 1, 0.5, 0.25 or even less than 0.1% acetate source;

(ii) an OAHS and/or OSHS content greater than 1, 10, 20, 50, 75 or even greater than 100 PPM;

(iii) a content of at least one particular impurity is greater than 1, 5 or even greater than 10 PPM; and (iv) carbon-14 to carbon-12 ratio of at least $2.0 \times 10^{-13}$.

In some embodiments, the composition includes less than 1.0, 0.8, 0.6, 04, 0.2 or even less than 0.1% organic acid or lesser or intermediate amounts.

Optionally, the composition is characterized by 2, 3, 4 or even all 5 of these characteristics.

Alternatively or additionally, the purity of the methionine is greater than 95, 96, 97, 98.5 or even 99% or intermediate or higher percentages.

Alternatively or additionally, the methionine includes less than 2, 1.5, 1, 0.5, 0.3 or even less than 0.1% of D-methionine. In some exemplary embodiments of the invention, the methionine is substantially enantiomerically pure.

Optionally, the L-methionine includes crystalline L-methionine.

In some exemplary embodiments of the invention, there is provided a complex comprising a composition as described above and a heavy metal.

In some exemplary embodiments of the invention, there is provided a feed or food composition comprising a composition as described above. According to various exemplary embodiments of the invention, this can be provided as a nutraceutical, a food product or an animal feed.

In some exemplary embodiments of the invention, there is provided a composition comprising L-methionine, characterized by at least one characteristic selected from the group consisting of:

(i) amino acids other than L-methionine in a concentration of at least 0.05, 0.08, 0.1, 0.15 or even 0.2% or more;

(ii) carboxylic acids in a concentration of at least 0.05, 0.08, 0.1, 0.15 or even 0.2% or more;

(iii) sulfate in a concentration of at least 0.2, 0.3, 0.4, 0.5, 0.7 or even 1% or more;

(iv) OAHS in a concentration of at least 1, 5, 10, 20, 50 or even 100 PPM or more; and (v) purity of at least 60, 65, 70, 75, 80 or even 85% or more.

In some exemplary embodiments of the invention, there is provided a composition comprising L-methionine, characterized by at least one characteristic selected from the group consisting of:

(i) a methionine concentration of at least, 15, 18, 21, 25, 28, 31 or even 35 g/l or more;

(ii) an acetate concentration of at least 140, 150, 160, 170, 180 or even 194 g/l or more;

(iii) total solids of at least 20, 23, 27, 30 or even 33% or more;

(iv) specific gravity in the range of 1.05 to 1.25, optionally between 1.1 and 1.2, optionally about 1.15; and (iv) ammonium sulfate concentration of at least 100, 110, 120, 130, 140 or even 150 g/l or more.

In some exemplary embodiments of the invention, there is provided a composition comprising L-methionine, characterized by at least one characteristic selected from the group consisting of:

(i) a methionine concentration of at least at least 100, 110, 120, 130, 140 or even 150 g/l or more;

(ii) an OAHS concentration less than 0.1% w/w;

(iii) a detectable amount of at least one amino acid selected from the group consisting of glutamic acid, valine, isoLeucine, leucine, tyrosine, phenylalanine and threonine;

(iv) a concentration of carboxylic acids other than acetic acid of 0.01, 0.02, 0.03, 0.04 or even 0.05 wt % or more; and (v) a methanol concentration of at least 10, 12, 14, 16 or even 18% or more by weight.

Optionally, this type of composition is provided as a crystallized slurry.

In some exemplary embodiments of the invention, there is provided a composition comprising:

(i) at least 30, 40, 50, 60, 70 or even 80% or more ammonium acetate;

(ii) at least 1, 5 or even 10 PPM or more of ammonium sulfate; and (iii) at least 1, 5 or even 10 PPM or more of a compound, optionally 2 compounds, optionally 3 compounds, selected from the group consisting of isobutanol, isobutyl acetate, acetamide and methionine.

In some exemplary embodiments of the invention, the above composition is provided as an ingredient of fermentation liquor.

In some exemplary embodiments of the invention, there is provided a composition comprising at least 30, 40, 50, 60, 70, 80, 85, 90 or even 95% or more ammonium sulfate, at least 1, 5 or 10 PPM or more of a compound, optionally at least 2 compounds, optionally at least 3 compounds selected from the group consisting of ammonium acetate, isobutanol, isobutyl acetate, acetamide and methionine. Optionally, the above composition is provided as an ingredient of a fertilizer.

In some exemplary embodiments of the invention, there is provided a composition comprising at least 90% isobutyl acetate, isobutanol and at least one of acetamide and acetic acid.

Exemplary Additional Reagents

Referring again to FIG. 2, additional reagents 124 are selected primarily to satisfy the requirements of enzymatic processing 120 which transforms OAHS or OSHS to methionine. Processing 120 has two main requirements.

In cases where OAHS is the L-methionine precursor, the first requirement of processing 120 is for methyl mercaptan as a co-substrate. Enzymatic conversion 120 of OAHS to methionine employs methyl mercaptan as a sulfur donor and the enzyme releases an acetyl group from the OAHS as a reaction product. Therefore, processing 120 requires that a source of methyl mercaptan be included in additional reagents 124.

The second requirement of processing 120 is an acidic environment to insure enzyme processivity and/or specificity.

In addition, there is a range of possible additional ingredients 124 which can be added and a selection of specific reagents 124 within that range can influence recovery of byproducts downstream both qualitatively and quantitatively.

According to various exemplary embodiments of the invention choice of a specific salt of methyl mercaptan to be included within additional reagents 124 to serve as a co-substrate for processing 120 influences a type and/or amount of downstream byproducts which can be recovered.

In some exemplary embodiments of the invention, use of ammonium-methyl mercaptan contributes to an ability to recover ammonia salts, such as ammonium sulfate and/or ammonium acetate, downstream. In other exemplary embodiments of the invention, use of calcium-methyl mercaptan contributes to an ability to recover calcium salts, including but not limited to calcium acetate and/or calcium sulfate downstream.

According to various exemplary embodiments of the invention, sulfuric acid or acetic acid are included within additional reagents 124 to provide an acidic environment for processing 120. In some exemplary embodiments of the invention, use of sulfuric acid contributes to an ability to recover sulfate salts, such as ammonium sulfate, downstream. In other exemplary embodiments of the invention, use of acetic acid contributes to an ability to recover acetate salts, including but not limited to ammonium acetate and/or calcium acetate, and/or to recover acetic acid downstream.

In some exemplary embodiments of the invention, inclusion of a strong acid, such as sulfuric acid, among additional reagents 124 contributes to a reduction in the burden on the process at extraction 310. In other exemplary embodiments of the invention, inclusion of a carboxylic acid, such as acetic acid, among additional reagents 124 contributes to an increase in the burden on the process at extraction 310.

Alternatively or additionally, inclusion of a strong acid, such as sulfuric acid, among additional reagents 124 contributes to a reduction in yield of primary L-methionine 180.

Exemplary Pre-Acidulation Treatment of a Purged Mother Liquor

FIG. 7 is a simplified flow diagram of a pre-acidulation treatment for a purged mother liquor indicated generally as 1200. Depicted exemplary method 1200 includes providing a purged mother liquor 1210 comprising ammonium acetate 1212 and contacting 1220 the liquor with lime to produce free ammonia 1224 and calcium acetate 1222. Optionally, the lime includes calcium oxide and/or calcium hydroxide.

The depicted exemplary embodiment includes contacting 1230 calcium acetate 1222 with an acid to precipitate a calcium salt 1232 of the acid and release acetic acid 1230. Optionally, acetic acid 1230 remains in solution.

Optionally, the acid used at 1230 is sulfuric acid and calcium salt 1232 is calcium sulfate (gypsum).

The depicted exemplary embodiment includes transforming 1240 acetic acid 1230 to an acetate salt 1250. In some exemplary embodiments of the invention, acetate salt 1250 is ammonium acetate.

Exemplary Extraction Strategy

Figure 8:
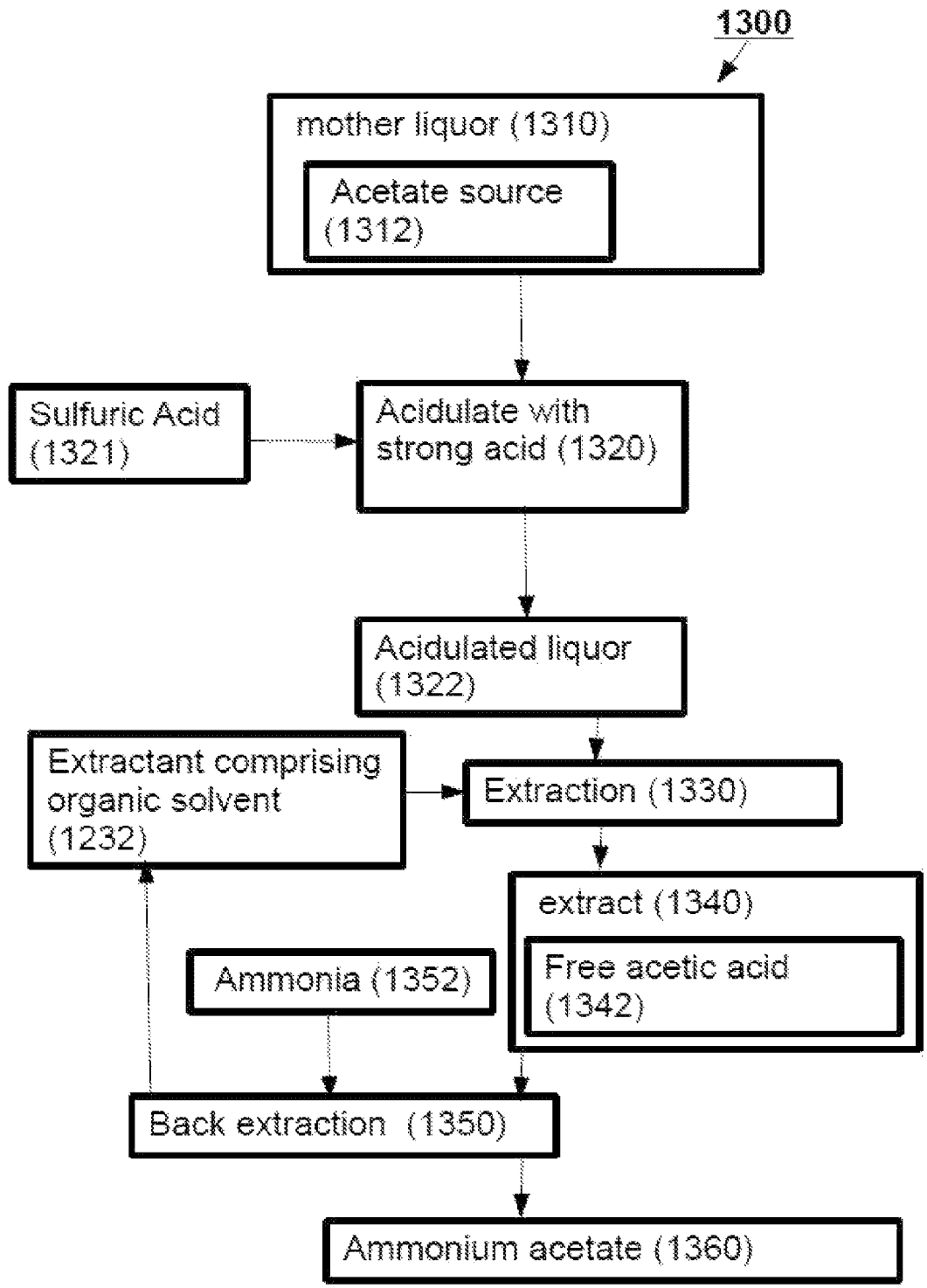
FIG. 8 is a schematic representation of a process for recovering ammonium acetate according to some exemplary embodiments of the invention.

FIG. 8 is a simplified flow diagram of a method for extracting acetate from a mother liquor indicated generally as 1300. Depicted exemplary method 1300 includes providing a mother liquor 1310 comprising an acetate source 1312. According to some exemplary embodiments of the invention, mother liquor 1310 is a purged mother liquor. Optionally, acetate source 1312 includes acetic acid and/or an acetate ester and/or an acetate salt.

Depicted exemplary method 1300 includes acidulating 1320 liquor 1310 with a strong acid to produce an acidulated liquor 1322. In the depicted embodiment, sulfuric acid 1321 serves as the strong acid.

Depicted exemplary method 1300 includes extracting 1330 acidulated liquor 1322 with an extractant 1232 including an organic solvent to produce an extract 1340 comprising acetic acid 1342. Optionally, the organic solvent includes isobutyl acetate (IBA).

Depicted exemplary method 1300 includes back-extracting 1350 extract 1340 with ammonia 1352 to produce ammonium acetate 1360 and regenerate extractant 1232.

In an alternate exemplary embodiment, back-extracting 1350 extract 1340 with water (not depicted) produces an aqueous solution of acetic acid (not depicted) and regenerates extractant 1232.

In an alternate exemplary embodiment (not depicted), distilling of extract 1340 is substituted for back extraction 1350. The distillation serves to separate acetic acid 1342 from extractant 1232 in extract 1340.

In another alternate exemplary embodiment (not depicted), extract 1340 is contacted with an alcohol to produce an acetate ester and regenerate extractant 1232. Optionally, the alcohol is ethanol and the ester is ethyl acetate. Optionally, the contacting comprises countercurrent extraction. Optionally, the countercurrent extraction includes 2, 3, 4 or 5 or more extraction stages.

It is expected that during the life of this patent many enzymes which convert OAHS and/or OSHS to methionine will be developed and the scope of the invention is intended to include all such new technologies a priori.

Alternatively or additionally, it is expected that during the life of this patent many microorganisms which produce enzymes OAHS and/or OSHS and/or microorganisms which convert these precursors to methionine will be developed and the scope of the invention is intended to include all such new technologies a priori.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Specifically, a variety of numerical indicators have been utilized. It should be understood that these numerical indicators could even vary further based upon a variety of engineering principles, materials, intended use and designs incorporated into the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are exemplary in nature and are not intended to limit the scope of the invention which is defined solely by the following claims. Specifically, the invention has been described in the context of production of L-methionine from OAHS and/or OSHS from bacterial fermentation but might also be used in parallel methods in which the methionine precursor is produced in cell culture and/or transgenic plants and/or transgenic animals.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

Additional objects, advantages, and novel features of various embodiments of the invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above description, illustrate the invention in a non limiting fashion.

Example 1

Methionine Production by Two Crystallization Steps

In order to examine the possibility of improving methionine yield, a fermentation liquor containing OAHS was enzymatically processed as described above and a two-stage crystallization was conducted.

Following the enzymatic processing, the liquor contained enzyme solution in volume ratio of 1.5%, methionine in a concentration of 70 g/l, OAHS in a concentration of 0.5 g/l, and methionine was separated from the liquor in a system including two crystallization steps. The first crystallization 150 treats a solution formed by combining the liquor with a recycle stream from second crystallization 220. Crystals formed in that first crystallization are referred to as first crystalline methionine. That first crystallization forms mother liquor (ML). Methionine is crystallized out of that mother liquor to form second crystalline methionine and second mother liquor referred to as purged mother liquor (PML). The second crystalline methionine is combined with methionine containing liquor to form the feed to the first crystallization.

The methionine liquor was mixed with the crystals from the second crystallization step. The pH was adjusted to 5 by the addition of sulfuric acid. The mixture was treated with active carbon to remove impurities and enzymes. The mixture was then concentrated by evaporation to methionine concentration of 150 g/l, followed by methanol aided crystallization in batch mode (methanol relative volume was 17% of the crystallization feed) by cooling from 55 to 25° C. and by using a crystal habit modifier (Tween 20). The crystals were washed and separated from the ML. The ML contained 25% of the methionine content in the first crystallization feed. After drying, the product crystals were formed and characterized. The results are summarized in Table 1. The ML was evaporated to recover the methanol (98.5% was recovered), followed by concentration by evaporation of the ML from 38 g/l of methionine to 150 g/l. It was then crystallized in a batch mode by cooling from 55 to 35° C. The crystals were washed and separated from the PML, and were mixed with the methionine liquor as described above. The PML contained 7% of the methionine contents in the first crystallization feed. Assuming recycling of second crystalline, the overall crystallization yield was 93%. The PML was analyzed and the results are summarized in Table 2.

Results presented in tables 1 and 2 indicate that the process can produce crystalline L-methionine of high purity.

This example illustrates that >92% of L-methionine produced by the enzymatic processing can be recovered as high purity crystals.

Figure 11:
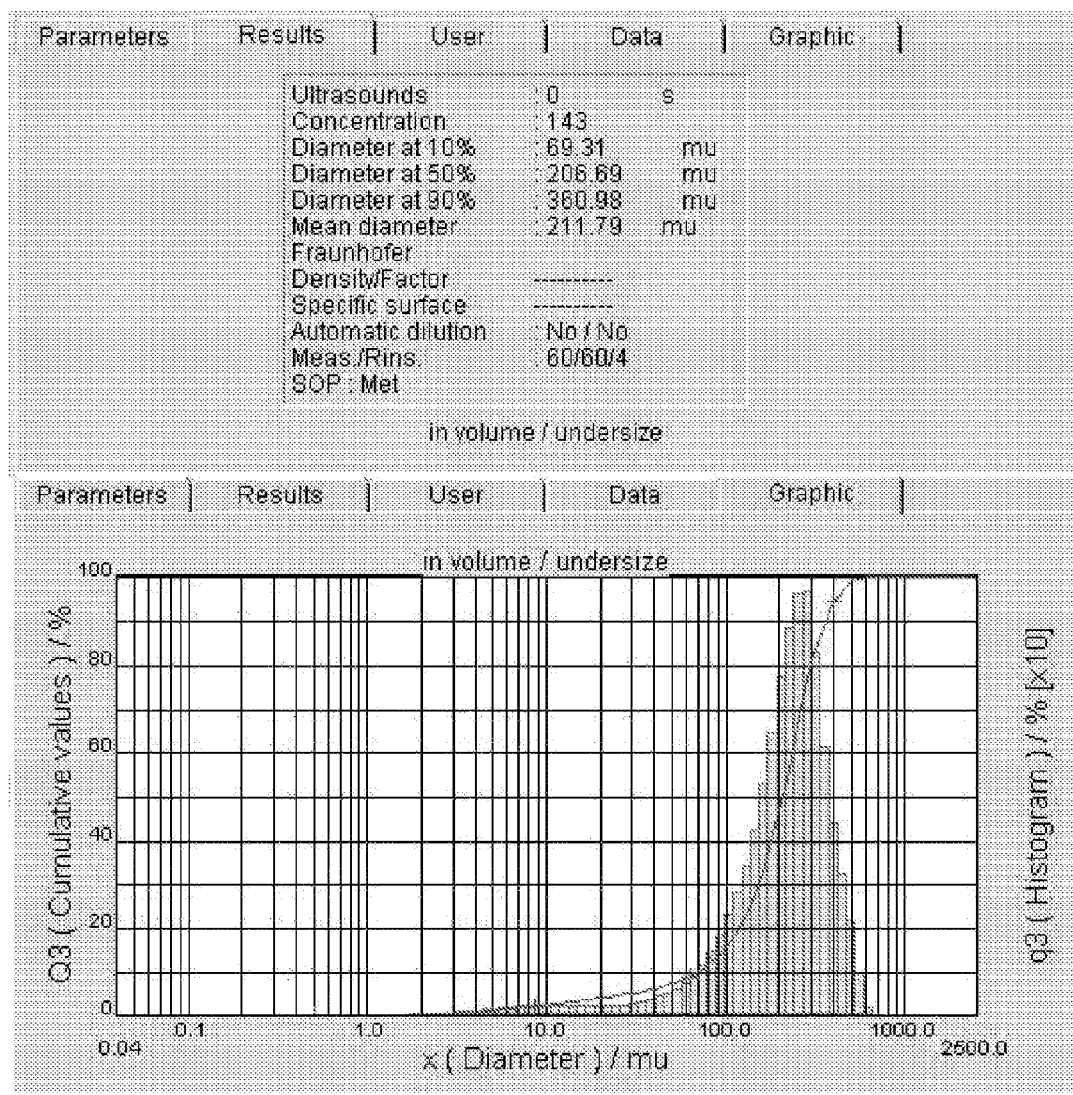
FIG. 11 shows the particle size distribution from example 1.

Particle size distribution from this example is shown in FIG. 11.

TABLE 1

| 1$^{st}$ crystals | |
|---|---|
| Composition: | |
| Amino acids | 0.2% |
| | (Phenylalanine 0.16%, Leucine 0.05%) |
| Carboxylic acids | ~0.01% (Acetic acid) |
| Sulfate | 0.02% |
| D-methionine | 0% |
| Purity | 99.2% |
| Bulk density | 50 g/dl |
| Crystals shape | Thin plate |

TABLE 2

| PML | |
|---|---|
| Total solids | 23 wt % |
| Composition: | |
| Methionine | 29 g/l |
| Acetate | 194 g/l |
| Ammonium | 5.5 wt % |
| Sulfate | 7.5 wt % |
| Specific gravity | 1.14 |

Example 2

Acetic Recovery from PML

In order to demonstrate the feasibility of recovering acetic acid from PML, the PML from Example 1 was first acidulated by adding sulfuric acid to reach pH 4 and then continuously extracted with IsoButyl Acetate (IBA) solvent in a counter current extractor. The number of stages of extraction was 10, Isobutyl acetate to PML ratio was 4:1 and the extractor temperature was 40° C. The extraction resulted in an organic phase loaded with acetic acid (extract) and in an acid-depleted aqueous phase (raffinate; e.g., aqueous phase 314). The extraction yield was 96%.

The organic phase and raffinate were analyzed and their compositions are presented in Tables 3 and 4, respectively. This example illustrates that acetic acid can be recovered from purged mother liquor by extraction with a suitable organic solvent.

Figure 12:
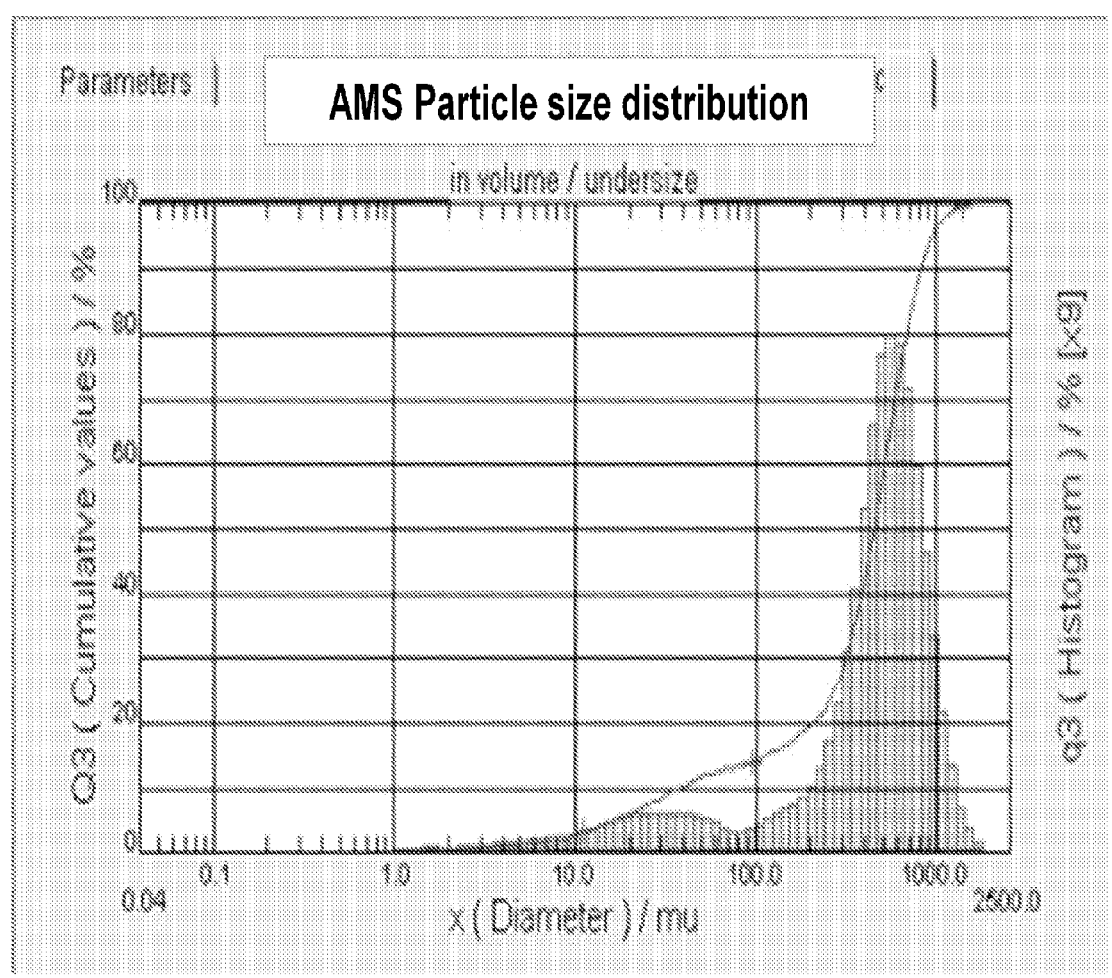
FIG. 12 shows the average particle size from example 2.

Average particle size from this example is shown in FIG. 12.

TABLE 3

| organic phase loaded with acetic acid (Loaded solvent) | |
|---|---|
| Composition: | |
| Acetic acid | 71 g/l |
| Moisture content | 2.9-% |
| Specific gravity | 1.05 |

TABLE 4

| Raffinate | |
|---|---|
| Composition: | |
| Methionine | 23 g/l |
| Acetate | 9 g/l |
| Ammonium sulfate | 27.3 wt % |
| Specific gravity | 1.19 |
| Total solids | 37% |

TABLE 5

| C-AmS | |
|---|---|
| Composition: | |
| Methionine | 3.3 wt % |
| AmS | 89.5 wt % |
| Moisture | 3% |
| Other | 4.2% |

TABLE 5-continued

| C-AmS | |
|---|---|
| Composition: | |
| Purity | 92.2% |
| Bulk density | 67 g/dl |
| Crystal shape | Cubic |
| Average particle size | 574 μm |
| | (See FIG. 12) |

Example 3

Ammonium Sulfate Recovery

In order to demonstrate the feasibility of recovering ammonia as a by-product, ammonium sulfate was crystallized from the raffinate of Example 2. 55% of the ammonium sulfate was separated as crystals and the remainder was left in an ammonium sulfate-containing mother liquor. The crystals were dried, and the dried crystals and ammonium sulfate mother liquor were analyzed. The results are presented in Tables 5 (above) and 6 (below), respectively. These results demonstrate that it is feasible to recover the bulk of the ammonium sulfate in a crystalline form.

TABLE 6

| L-AmS(Liquid fertilizer) | |
|---|---|
| Composition: | |
| Methionine | 3.0 wt % |
| Ammonia | 6.7 wt % |
| Other | 35.3 wt % |
| Specific gravity | 1.25 |
| Total solids | 46 wt %% |

Example 4

Ammonium Acetate Recovery

In order to demonstrate the feasibility of recovering ammonium acetate, 300 ml of loaded extractant formed in Example 2 was mixed with 35 ml of aqueous solution containing 25% ammonia. Contacting was in a single stage. After phase separation, 56 ml of aqueous solution was recovered. The contactor temperature was 34° C. A regenerated extractant and an aqueous solution of ammonium acetate were formed. The composition of the formed aqueous solution is presented in table 7.

TABLE 7

| Ammonium acetate | |
|---|---|
| Composition: | |
| Methionine | N/D |
| Ammonium acetate | 52.6 wt % |
| SO4-2 | 0.01 wt % |
| K+ | 0.04 wt % |
| Specific gravity | 1.107 |

Example 5

IBA Stability in Back-Extraction Conditions

In order to establish the feasibility of recycling an extractant containing IBA, IBA stability was tested at back-extraction conditions over extended time. A 50% aqueous ammonium acetate solution was prepared. The pH of the solution was adjusted to 9.6 by the addition of a 24% ammonia solution. That aqueous solution was mixed with isobutyl acetate at 30° C. for 6 and 14 days. Samples from the isobutyl acetate phase were taken for analysis of isobutyl alcohol. The results show an average solvent hydrolysis rate of 0.045% per day. These results suggest that recycling of an IBA extractant is feasible.

Example 6

Acetic Acid Recovery by Distillation

In order to examine the feasibility of recovering acetic acid by distillation, PML from Example 1 was acidulated by adding sulfuric acid to form acidulated PML (APML) of pH 4. The APML was heated to boiling and the vapors were collected and analyzed. The condensate was found to be an aqueous solution containing acetic acid in a concentration of 14.5 wt %. Composition of the condensate is summarized in Table 8. This example illustrates that it is feasible to recover acetic acid as a solution of at least 14.5 wt % by distilling an APML.

TABLE 8

Acetic acid condensate

| Composition: | Concentration |
|---|---|
| Methionine | N/D |
| Acetic acid | 14.5 w % |
| NH4+ | 7 ppm |
| PO4-3 | 53 ppm |
| SO4-2 | 120 ppm |

Example 7

OAHS Fermentation Using Recovered Ammonium Acetate

A bacterial strain of interest that produces substantial amounts of O-acetyl-L-homoserine was subsequently tested under production conditions in a 5 L fermentor (New Brunswick Scientific, New Brunswick, N.J.) using a fed batch strategy.

E. coli KCCM 10921P mutant strain was used as seed strain. The E. coli KCCM 10921P was propagated by being transferred from LB agar plate to 500 ml baffled Erlenmeyer flasks containing 50 ml of flask culture medium in which the cells were cultured with shaking under sufficient aeration at 30 to 37° C. for 6 hours.

50 ml of flask culture broth was inoculated in a 1 L fermentor containing 500 ml of seed medium, followed by culture at 30 to 37° C., 900 rpm for 5 to 15 hours.

300 ml of the seed culture broth was transferred to a 5 L fermentor containing 1.8 L of the main medium. The main culture was subjected to batch growth at 30 to 37° C. until residual glucose concentration of 20 g/L was obtained. Thereafter, the feed media (with or without ammonium acetate) supply was started and the fed-batch fermentation was performed at 30 to 37° C., 900 rpm for 30 to 100 hours.

Table 9 shows compositions of flask media, seed media, feed without ammonium acetate and feed with ammonium acetate.

TABLE 9

Fermentation medium composition for O-acetyl-L-homoserine production

| Composition | Flask media | Seed media | Main media | Feed (W/O Ammonium acetate) | Feed (With Ammonium acetate) |
|---|---|---|---|---|---|
| Glucose (g/L) | 2 | 101 | 40 | 605 | 515 |
| MgSO$_4$•7H$_2$O (g/L) | 0.5 | 0.5 | 4.2 | | |
| Yeast extract (g/L) | 10 | 10 | 3.2 | | |
| KH$_2$PO$_4$ | 3 | 3 | 3 | 8 | 8 |
| Ammonium sulfate (g/L) | | | 6.3 | | |
| Ammonium acetate (g/L) | | | | | 127 |
| NH$_4$Cl (g/L) | 1 | 1 | | | |
| NaCl (g/L) | 0.5 | 0.5 | | | |
| Na$_2$HPO$_4$•12H$_2$O (g/L) | 12.3 | 5.07 | | | |
| DL-Methionine (g/L) | 0.1 | | 0.5 | 0.5 | 0.5 |
| L-Isoleucine (g/L) | 0.05 | 0.05 | 0.5 | 0.5 | 0.5 |
| L-Threonine (g/L) | 0.1 | | 0.5 | 0.5 | 0.5 |

The resultant O-acetyl-L-homoserine concentration in the fermented solution was measured by HPLC and the results are shown in Table 10.

TABLE 10

O-acetyl-L-homoserine production in a fermentor

| Strain | Carbon sources | O-acetyl-L-homoserine (g/L) | Carbon yield (%)* |
|---|---|---|---|
| E. coli KCCM 10921P | Sucrose | 135.0 | 53.2 |
| | Sucrose with ammonium acetate | 136.1 | 54.0 |

*Carbon Yield (%) = O-Acetyl-L-Homoserine (g (Carbon))/Sucrose (g (Carbon)) + Ammonium acetate (g (Carbon))

These results indicate that adding ammonium acetate to the feed can reduce the sugar requirement of the fermentation more than 15% without adversely affecting carbon yield.

What is claimed is:

1. A method for producing an L-methionine product comprising;
    (a) providing a fermentation liquor comprising an L-methionine precursor selected from the group consisting of O-acetylhomoserine (OAHS) and O-succinyl homoserine (OSHS), and at least one impurity;
    (b) enzymatically processing said precursor to produce a reaction liquor comprising L-methionine, an organic acid selected from the group consisting of acetic acid and succinic acid and at least one impurity;
    (c) modifying said reaction liquor to form a crystallizing feed;
    (d) crystallizing L-methionine from said crystallizing feed to form crystalline L-methionine and an L-methionine-depleted mother liquor; and
    (e) recovering at least a portion of said organic acid from said mother liquor as recovered organic acid; wherein said recovering comprises producing a residual liquor containing said free organic acid and separating said free organic acid, and said crystalline L-methionine is characterized by at least one characteristic selected from the group consisting of:
(i) purity greater than 95%;
(ii) containing less than 1% organic acid;
(iii) L-methionine precursor content greater than 1 PPB;
(iv) content of at least one particular impurity is greater than 10 PPM;
(v) less than 2% of D-methionine; and
(vi) carbon-14 to carbon-12 ratio of at least $2.0 \times 10^{-13}$.

2. The method according to claim 1, wherein said modifying comprises combining said reaction liquor with an L-methionine-comprising recycle stream.

3. The method according to claim 2, further comprising the step of separating L-methionine from said mother liquor to form said L-methionine-comprising recycle stream and a purged mother liquor stream.

4. The method according to claim 3, wherein said separating L-methionine from said mother liquor comprises crystallizing to form second crystalline L-methionine and separating said second crystalline L-methionine from said purged mother liquor.

5. The method according to claim 1, wherein one or more of said impurity is selected from the group consisting of amino acids, vitamins, minerals, ammonia, acetic acid, succinic acid, methyl mercaptan, enzymes, L-methionine precursor and a combination thereof.

6. The method according to claim 1, wherein said L-methionine precursor is O-succinyl homoserine, wherein said organic acid is succinic acid and wherein said processing is conducted in the presence of calcium ions.

7. A method for producing an L-methionine comprising;
(a) enzymatically processing a fermentation liquor comprising an L-methionine precursor selected from the group consisting of O-acetylhomoserine (OAHS) and O-succinylhomoserine (OSHS) to produce L-methionine and a source of an organic acid selected from acetic acid and succinic acid;
(b) separating at least a portion of said L-methionine from at least a fraction of said source of organic acid to form separated L-methionine and a residual liquor comprising the source of organic acid; and
(c) recovering at least a portion of said source of organic acid from said residual liquor as recovered organic acid, wherein said recovering comprises producing said residual liquor containing free organic acid and separating said free organic acid.

8. The method according to claim 7, further comprising using said recovered organic acid as a reagent, wherein said using comprises applying to production of a fermentation product.

9. The method according to claim 8, wherein said fermentation product is selected from the group consisting of carboxylic and amino acids.

10. The method according to claim 7, further comprising using said recovered organic acid as a reagent, wherein said using comprises adding said reagent as an ingredient in a fermentation medium.

11. The method according to claim 7, wherein said L-methionine precursor is O-succinyl homoserine, wherein said organic acid is succinic acid, and wherein recovering comprises forming residual liquor comprising free succinic acid and separating said free succinic acid.

* * * * *